United States Patent [19]
Sriram et al.

[11] Patent Number: 6,045,796
[45] Date of Patent: Apr. 4, 2000

[54] VACCINATION WITH PEPTIDE OF MHC CLASS II MOLECULES FOR TREATMENT OF AUTOIMMUNE DISEASE

[75] Inventors: Subramaniam Sriram, Nashville, Tenn.; Bishwajit Nag, Fremont; Somesh D. Sharma, Los Altos, both of Calif.

[73] Assignee: Anergen, Inc., Redwood City, Calif.

[21] Appl. No.: 08/485,617

[22] Filed: Jun. 7, 1995

Related U.S. Application Data

[63] Continuation-in-part of application No. 08/338,553, Nov. 18, 1994, which is a continuation-in-part of application No. 07/992,942, Dec. 17, 1992, abandoned.

[51] Int. Cl.$^7$ .............................. A61K 39/00; C07K 14/74
[52] U.S. Cl. .................................... 424/185.1; 424/184.1; 530/300; 530/395
[58] Field of Search .................................... 530/300, 350, 530/395, 868; 424/185.1

[56] References Cited

U.S. PATENT DOCUMENTS

| | | |
|---|---|---|
| 5,130,297 | 7/1992 | Sharma . |
| 5,194,425 | 3/1993 | Sharma . |

FOREIGN PATENT DOCUMENTS

| | | |
|---|---|---|
| 0 068 790 | 1/1983 | European Pat. Off. . |
| 0 286 447 | 10/1988 | European Pat. Off. . |
| 0 286 447 | 10/1998 | European Pat. Off. . |
| 91/01133 | 2/1991 | WIPO . |
| 92/16234 WO | 10/1992 | WIPO . |
| 92/169234 | 10/1992 | WIPO . |

OTHER PUBLICATIONS

Acha–Orbea, H. et al., "T cell receptors in murine autoimmune disease"*Ann Rev. Immunol.*7:371–405 (1989).

Adorini, L. et al., "*In vivo*competition between self peptides and foreign antigens in T–cell activation"*Nature*334:623–625 (1988).

Agrawal, B. et al., "T Cells That Recognize Peptide Sequences of Self MHC Class II Molecules Exist in Syngenic Mice"*J. Immunol.* 147 (2) :383–390 ( 1991).

Aharoni, R. et al., "Immunomodulation of experimental allergic encephalomyelitis by antibodies to the antigen–la complex"*Nature*351:147–150 (1991).

Anderson, D.C. et al., "A *Mycobacterium leprai*–Specific Human T Cell Epitope Cross–Reactive with an HLA–DR2 Peptide"*Science*242:259–261 (1998).

Benichuo, G et al., "Immunogenicity and Tolerogenicity of Self–Major Histocampatibility Complex Peptides"*J. Exp. Med.* 172:1341–1346 (1990).

Blasczyk, R. et al., "Soluble CD4, CD8, and HLA molecules in commerical immunoglobulin preparations"*The Lancet*341:798–790 (1993).

Bright, J.J. et al., "Vaccination with peptides from MHC class II beta chain hypervariable region causes allete–specific suppression of EAE"*J. Neuroimmunol.*67:119–124 (1996).

Brown, J.H. et al., "Three–dimesional struture of the human class II histocampatibility antigen HIA–DR1"*Nature*364:33–39 (1993).

Cohran, R.S. et al., eds., *Robbin'Pathological Basis of Disease*, 4th ed., Chapter 5, pp. 163–236 (1989).

German, R.N., *Fundamental Immunology*, 3rd edition, (W.E. Paul, ed.) Chapter 17, "The major Histocompatibility Complex"pp. 629–676 (1993).

Goodman, J.W., "Immunogenicity & Antigenic Specificity"in: *Fundamental Immunology*, pp. 101–108 (1991).

Gorga, J.C., "Structural Analysis of Class II Major histocompatibility Complex Proteins"*Crit. Rev. Immunol.* 11 (5) :305–335 (1992)T.

Hansen, T.H. et al., *Fundamental Immunology*, 3rd edition, (W.E. Paul, ed.) Chapter 16, "The Major Histocompatibility Complex"pp. 577–628 (1993).

Howell, M.D. et al., "Vaccination against experimental allergic encephalomyelitis with T–cell receptor peptides"*Science*246:668–670 (1989).

Kwak, L.W. et al., "Induction of Immune Responses in Patients With B–Cell Lymphomas, The Surface–Immunoglobulin Idiotype Expressed By Their Tumors", *New Engl. J. Med.* 327(17) :1209–1215 (1992).

Lamont, A.G. et al., "Inhibition of experimental autoimmune encephalomyelitis induction in SJL/J mice by using a peptide with high affinity for IA$^s$molecules"*Science*246:2527–2531 (1992).

Li, H.F. et al., "Modulation of restricted class II T–cell responses by peptides derived from self class II molecule"*Eur. J. Immunol.* 22:2527–2531 (1992).

Margulise, D.H. et al., "Engineering Soluble Major Histocompatibilty Molecules: Why and How"*Immunol. Res.* 6: 101–116 (1987).

Mazerolles, F. et al., "Immunosuppressive Properties of Synthetic Peptides Derived from CD4 and HLA–DR Antigens"*Cell*55:497–504 (1988).

Moretta, A. et al., "Involvement of T44 Molecules in an Antigen–Independent Pathway of T Cell Activation"*J. Exp. Med.* 162:823–838 (1985).

(List continued on next page.)

Primary Examiner—Thomas M. Cunningham
Attorney, Agent, or Firm—Townsend and Townsend and Crew LLP

[57] ABSTRACT

The present invention provides immunogenic oligopeptides derived from the Major Histocompatibility Complex (MHC) glycoprotein protein sequences for use in compositions and methods for the treatment, prevention and diagnosis of deleterious immune responses, such as autoimmunity and allergies. The peptides are capable of inducing an immune response against glycoproteins encoded MHC alleles associated with the target disease. In preferred embodiments the peptides of the invention are derived from hypervariable region of the β chain of an MHC Class II molecule associated with the deleterious immune response.

35 Claims, 8 Drawing Sheets

OTHER PUBLICATIONS

Muller, S. et al., "Selective in vivo Inhibition of T-cell Activation by Class II MHC-Binding Peptides Administered in Soluble Form"*J. Immunol.* 145(12) :4006–4011 (1990).

Nicolle, M.W. et al., "Specific tolerence to an acetylcholine receptor epitope induced in vitro in myasthenia gravis CD4+ lymphocytes by soluble MHC class II–peptide complexes"*J. Clin. Invest.* 93:1361–1369 (1994).

Parham, P., "Peptide feeding and cellular cookery"*Nature*30:793–795 (1990).

Ploegh, H. et al., "MHC class II dimer of dimers"*Nature*364:16–17 (1993).

Roudier, J. et al., "Tolerance to self peptide from the third hypervariable region of the $E^s$ chain. Implications for molecular mimicry models of autoimmune disease"*Eur. J. Immunol.* 21:2063–206 (1991).

Roudier, J. et al., "Immune response to peptides from the third hypervariable region of the β chain of MHC class II molecules. Implications for the immune response to foreign antigens"*Cancer Biol.* 2:283–285 (1991).

Saskia, H. et al., "T Cells Sensitized To Synthetic HLA–DR3 Peptide Give Evidence of Continouos Presentation of Denatured HLA–DR3 Molecules by HLA–DP"*J. Exp. Med.* 169:1191–1196 (1989).

Schneck, J. et al., "Inhibition of an allospecific T cell hybridoma by soluble class I proteins and peptides: Estimation of the affinity of a T cell receptor for MHC"*Cell*56:47–55 (1989).

Schwartz, R.S., *Fundamental Immunology*, 3rd edition (W.F. Paul, ed.), Chapter 30 "Autoimmunity and Autoimmune Disease"pp. 1033–1095 (1993).

Sharma, S. et al., "Antigen-specific therapy of experimental allergic encephalomyelitis by solube class II Major histocompatibility complex–peptide complexes"*Proc. Natl. Acad. Sci. USA*88:11465–11469 (1991).

Sigal, N.H. et al., Fundamental Immunology , 3rd edition, (W.E. Paul, ed.) Chapter 25, "Immunosuppression"pp. 903–915 (1993).

Sriram, S. and Steinman, L., "Anti I–A antibody suppresses active encephalomyelitis: Treatment model for diseases linked to IR genes"*J. Exp. Med*158:1362–1367.

Steinman, L. et al., "In vivo effects of antibodies to immune response gene products: Prevention of expermental allergic encephalitis"*Proc. Natl. Acad. Sci. USA*78(11):7111–7114 (1981).

Steinman, L. "The Development of Rational Strategies for Selective Immunotherapy against Autoimmune Demyelinating Disease"*Adv. Immunol.* 49:357–379 (1991).

Topham, D.J. et al. "A sythetic peptide from the third hypervariable region of MHC class II βchain as a vaccine for treatment of experimental allergic encephalomyelitis"*Proc. Natl. Acad. Sci.* USA 91–8005–8009 (1994).

Vandenbark, A.A. et al., "Immunization with a synethia T–cell receptor V–region peptide protects against experimental autoimmune encephalomyelitis"*Nature*341:541–544.

Vladutiu, A.O. and Steinman, L., "Inhibition of experimental autoimmune thyroiditis in mice by anti–I–A antibodies"*Cell Immunol.* 109:169–180.

Waldor, M.K. et al., "*In vivo*therapy with monoclonal anti–I–A–antibody suppresses immune respones to acetylcholine receptor"*Proc. Natl. Acad. Sci. USA*. 80:2713–2717 (1983).

Winkelhake, J.L. et al., "Therapeutic Peptide Vaccines: Targeting the Antigen–recognition Unit in Autoimmune Diseases"*Vaccine Res.* 5(3) :119–135 (1996).

Wooley, P.H. et al., "Type II collgen–induced arthritis in mice: Suppression of arthritis by using monoclonal and polyclonal anti–Ia antisera"*J. Immunol.* 134 (4):2366–2374 (1995).

Wraith, D.C. et al/. "T cell recognition as the target for immune intervention in autoimmune disease"*Cell*57:709–715 (1989).

Zaller, D.M. et al., "Prevention and treatment of murine experimental allergic encephalomyelitis with T cell receptor Vβ–specific antibodies"*J. Exp. Med.* 171:1943–1955 (1990).

Nancy E. Adelman et al. "TREATMENT OF (NZB X NZW) F $^1$DISEASE WITH ANTI–I–A MONOCLONAL ANTIBODIES", Brief Definitive Report, 158:1350–1355 (1983).

C. Boitard et al., "PREVENTION OF DIABETES IN NON-OBESE DIABETIC MICE BY ANTI–I–A MONOCLONAL ANTIBODIES: TRANSFER OF PROTECTION BY SPLENIC T CELLS", Proc, Natl. Acad. Sci. USA. 85:9719–9723 (1988).

J. Lee Nelson et al., "MATERNAL–FETAL DISPARITY IN HLA CLASS II ALLOANTIGENS AND THE PREGNANCY–INDUCED AMELIORATION OF RHEUMATOID ARTHRITIS", The New England Journal of Medicine pp. 466–471 (Aug. 12, 1993).

Sophie Salvat et al., "TOLERANCE TO A SELF–PEPTIDE FROM THE THIRD HYPERVARIABLE REGION OF HLA DRB1 0401 IN RHEUMATOID ARTHRITIS PATIENTS AND NORMAL SUBJECTS", The American Association of Immunologists pp. 5321–5329 (1994).

Roudier, J., et al. (1991) "Tolerance to self peptide from the third hypervariable region of the $E^s_\beta$chain. Implications for molecular mimicry models of autoimmune disease", *Eur. J. Immunol.*, 21:2063–2067.

Sharma, Somesh D., et al. (1991) "Antigen–specific therapy of experimental allergic encephalomyelitis by soluble class II major histocompatibility complex–peptide complexes", *Proc. Natl. Acad. Sci. USA*, 88:11465–11469.

HPTYP

| # | FREQ % | DQ | DQB1 | DQA1 | DRB1 | DRB3 | DRB4 | D | DISEASE ASSOCIATION |
|---|---|---|---|---|---|---|---|---|---|
| 1 | 20 | w5(w1) | 1.1 | 1a | 1 | ne | ne | w1 | IDDM(MAJOR), RA(MINOR) |
| 2 |  | w5(w1) | 1.1 | 1a | 1 | ne | ne | w20 |  |
| 3 | 26 | w6(w1) | 1.2 | 1b | w15(2) | ne | ne | w2 | CPMS, MG(T+) |
| 4 | 1.5 | w6(w1) | 1.12 | 1c | w15(2) | ne | ne | w12 | IDDM(-) |
| 5 | 1.5 | w5(w1) | 1.1 | ? | w16(2) | ne | ne | w21(AZH) | IDDM(+), MG(T-) |
| 6 | ? | w7(w3) | 3.1 | ? | w16(2) | ne | ne | w22 |  |
| 7 | 22 | w2 | ? | ? | w17(3) | 24(52) | ne | w3 |  |
| 8 |  | w2 | ? | ? | w17(3) | 25(52) | ne | w3 | IDDM(+), MG(T-) |
| 9 | ? | w4(Wa) | Wa | ? | w18(3) | ?(52) | ne | ? |  |
| 10 | 9 | w8(w3) | 3.2 | 3 | 4 | ne | 53 | w4(4.2) | IDDM*(+)(MAJOR), RA† (MAJOR), CPMS |
| 11 | 5 | w7(w3) | 3.1 | 3 | 4 | ne | 53 | w4(4.1) |  |
| 12 | 3 | w8(w3) | 3.2 | 3 | 4 | ne | 53 | w10 | IDDM*(+)(MAJOR), CPMS |
| 13 | ? | w7(w3) | 3.1 | 3 | 4 | ne | 53 | w13 |  |
| 14 | 14 | w8(w3) | 3.2 | 3 | 4 | ne | 53 | w14 | IDDM*(+)(MAJOR), RA† (MAJOR), CPMS |
| 15 | 0.5 | w4(Wa) | Wa | ? | 4 | ne | 53 | w15 |  |
| 16 | 15 | w7(w3) | 3.1 | 2 | w11(5) | 25(52) | ne | w5 |  |
| 17 |  | w7(w3) | 3.1 | 2 | w12(5) | 25(52) | ne | B6 |  |
| 18 | 10 | w5(w1) | 1.18 | 1c | w(13)(w6) | 24(52) | ne | w18 |  |
| 19 |  | w5(w1) | 1.18 | 1c | w(13)(w6) | 25(52) | ne | w18 |  |
| 20 | 3 | w5(w1) | 1.19 | 1b | w(13)(w6) | 26(52) | ne | w19 | IDDM(MINOR) |
| 21 | 3 | w6(w1) | 1.9 | 1a | w(14)(w6) | 25(52) | ne | w9 |  |
| 22 | ? | w6(w1) | 1.16 | 2 | w(14)(w6) | 24(52) | ne | w16 | RA(MINOR) |
| 23 | 1 | w9(w3) | 3.3 | 3 | 7 | ne | 53 | w11 |  |
| 24 | 27 | w2 | 2 | 3 | 7 | ne | 53 | w17 |  |
| 25 | 6 | w4(Wa) | Wa | 1b | ne | w8/52 | ne | w8 |  |
| 26 | 2 | ?(w3) | ? | 1b | ne | w8/52 | ne | w8 |  |
| 27 | 1 | w9(w3) | 3.3 | 3 | 9 | ne | 53 | w23 |  |
| 28 | ? | w5(w1) | 1.1 | 1a | w10 | ? | ? | ? |  | ne: NOT EXPRESSED  
T-: THYMOMA-NEGATIVE  
T+: THYMOMA-POSITIVE  
CPMS: CHRONIC-PROGRESSIVE MULTIPLE SCLEROSIS  
IDDM: INSULIN-DEPENDENT DIABETES MELLITUS  
MG: MYASTHENIA GRAVIS  
RA: RHEUMATOID ARTHRITIS

VACCINATION WITH PEPTIDE OF MHC CLASS II MOLECULES FOR TREATMENT OF AUTOIMMUNE DISEASE

This application is a Continuation-in-Part of U.S. Ser. No. 08/338,553, filed Nov. 18, 1994, which is a Continuation-in-Part of U.S. Ser. No. 07/992,942, filed Dec. 17, 1992 (now abandoned), the disclosure of which is incorporated herein by reference.

BACKGROUND OF THE INVENTION

The present invention relates to novel compositions and methods for inhibiting immune responses associated with autoimmune diseases and allergic responses. In particular, it relates to vaccination with peptides from, for instance, the hypervariable region of MHC molecules encoded by alleles associated with disease.

A number of pathological responses involving unwanted immune responses are known. For instance, a number of allergic diseases, have been associated with particular MHC alleles or suspected of having an autoimmune component. Other deleterious T cell-mediated responses include the destruction of foreign cells that are purposely introduced into the body as grafts or transplants from allogeneic hosts. This process, known as "allograft rejection," involves the interaction of host T cells with foreign MHC molecules. Quite often, a broad range of MHC alleles are involved in the response of the host to an allograft.

Autoimmune disease is a particularly important class of deleterious immune response. In autoimmune diseases, self-tolerance is lost and the immune system attacks "self" tissue as if it were a foreign target. More than 30 autoimmune diseases are presently known; these include many which have received much public attention, including myasthenia gravis (MG) and multiple sclerosis (MS).

A crude approach to treating autoimmune disease and other immunopathologies is general immunosuppression. This has the obvious disadvantage of crippling the ability of the subject to respond to real foreign materials to which it needs to mount an immune response. Recent approaches to treating autoimmune disease have involved the use of peptides having an amino acid sequence encoded by a T-cell receptor V gene. The peptides have been proposed as vaccines for preventing, suppressing and treating immune related diseases (see, International Application No. WO 91/01133. Another approach involves the use of monoclonal antibodies against MHC gene products. The antibodies have been proposed for use in targeting cell bearing MHC molecules associated with particular diseases (see, EP Publication No. 68790).

These prior art methods fail to provide a simple self-mediated method for specifically eliminating immune responses restricted by glycoproteins encoded by MHC alleles associated with a variety of deleterious immune responses. Such methods can be used to prevent and/or suppress diseases, particularly those in which the antigen or allergen is not known.

SUMMARY OF THE INVENTION

The present invention relates to methods and compositions for inhibiting deleterious immune responses. The compositions of the invention comprise an isolated immunogenic MHC polypeptide. The immunogenic MHC polypeptide is usually from a hypervariable region in a Class II molecule. Hypervariable regions from Class II β chains are typically used. The polypeptides are used to induce an immune response against the target sequence of the MHC molecule, thereby rendering the MHC molecules ineffective in initiating the deleterious immune response.

The MHC molecule can be associated with autoimmune disease, such as multiple sclerosis. Alternatively, it may be associated with an allergic response, to a number of allergens, such as ragweed.

The invention also provides pharmaceutical compositions comprising the polypeptides. The compositions can be used for the treatment of autoimmune diseases or allergic responses. The compositions can be administered prophylactically or after the condition has been diagnosed.

DEFINITIONS

The term "peptide" is used interchangeably with "oligopeptide" or "polypeptide" in the present specification to designate a series of residues, typically L-amino acids, connected one to the other typically by peptide bonds between the α-amino and carbonyl groups of adjacent amino acids.

An "immunogenic MHC polypeptide" or of the present invention is a polypeptide capable of eliciting an immune response against an MHC molecule associated with a deleterious immune response in a patient. As set forth in more detail below, the sequence of residues in the polypeptide will be identical to or substantially identical to a polypeptide sequence in the MHC molecule. Thus, a polypeptide of the invention that has a sequence "from a region in an MHC molecule" (e.g., the hypervariable region) is polypeptide that has a sequence either identical to or substantially identical to the naturally occurring MHC amino acid sequence of the region. Typically, the polypeptide sequence in the MHC molecule will be from a hypervariable region.

As used herein a "hypervariable region" of an MHC molecule is a region of the molecule in which polypeptides encoded by different alleles at the same locus have high sequence variability or polymorphism. The polymorphism is typically concentrated in the α1 and α2 domains of in Class I molecules and in the α1 and β1 domains of Class II molecules. The number of alleles and degree of polymorphism among alleles may vary at different loci. For instance, in HLA-DR molecules all the polymorphism is attributed to the β chain and the α chain is relatively invariant. For HLA-DQ, both the α and β chains are polymorphic.

The phrases "isolated" or "biologically pure" refer to material which is substantially or essentially free from components which normally accompany it as found in its native state. Thus, the MHC polypeptides of this invention do not contain materials normally associated with their in situ environment, e.g., other surface proteins on antigen presenting cells. Even where a protein has been isolated to a homogenous or dominant band, there are trace contaminants in the range of 5–10% of native protein which co-purify with the desired protein. Isolated polypeptides of this invention do not contain such endogenous co-purified protein.

The term "residue" refers to an amino acid or amino acid mimetic incorporated in a oligopeptide by an amide bond or amide bond mimetic.

BRIEF DESCRIPTION OF THE DRAWINGS

FIG. 1 provides a list of the DQ/DR haplotypes in humans and their associations with autoimmune diseases.

FIG. 3A shows the results of ELISA binding assays of antibodies obtained from animals immunized with the 10mer peptide.

DESCRIPTION OF THE PREFERRED EMBODIMENTS

Figure 2:
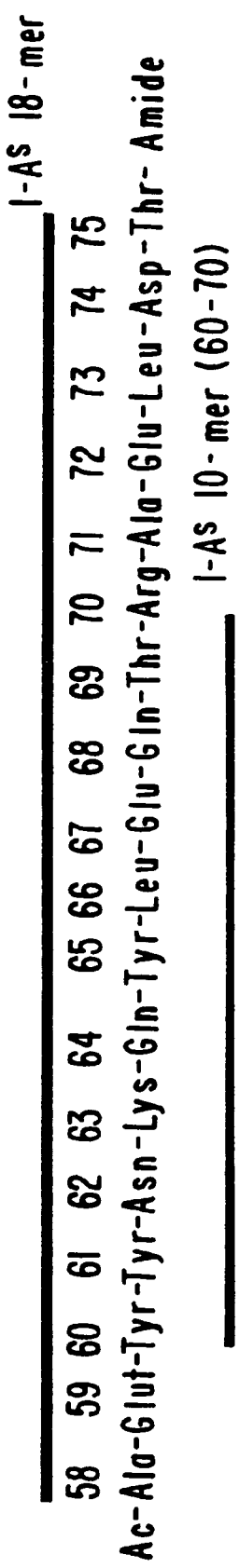
FIG. 2 shows the location of two peptides I-A$^s$β p18mer and I-A$^s$βp10mer and their location in the third hypervariable region of the β chain of I-A$^s$.

The present invention provides immunogenic polypeptides derived from the Major Histocompatibility Complex (MHC) glycoprotein protein sequences for use in compositions and methods for the treatment, prevention and diagnosis of deleterious immune responses. The polypeptides are capable of inducing an immune response against glycoproteins encoded by MHC alleles associated with the target disease. In preferred embodiments the polypeptides of the invention are derived from hypervariable regions of the α or β chain of an MHC Class II molecule associated with the deleterious immune response. In this way, the ability of antigen presenting cells (APC) to present the target antigen (e.g., autoantigen or allergen) is inhibited.

The glycoproteins encoded by the MHC have been extensively studied in both the human and murine systems. Many of the histocompatibility proteins have been isolated and characterized. For a general review of MHC glycoprotein structure and function, see *Fundamental Immunology*, 3d Ed., W. E. Paul, ed., (Ravens Press N.Y. 1993).

MHC molecules are heterodimeric glycoproteins expressed on cells of higher vertebrates and play a role in immune responses. In humans, these molecules are referred to as human leukocyte antigens (HLA). MHC glycoproteins are divided into two groups, class I and class II, which differ structurally and functionally from each other. In general, the major function of MHC molecules is to bind antigenic peptides and display them on the surface of cells.

Class I MHC molecules are expressed on almost all nucleated cells and are recognized by cytotoxic T lymphocytes, which then destroy the antigen-bearing cells. Class II MHC molecules are expressed primarily on cells involved in initiating and sustaining immune responses, such as T lymphocytes, B lymphocytes, macrophages, and the like. Class II MHC molecules are recognized by helper T lymphocytes and induce proliferation of helper T lymphocytes and amplification of the immune response to the particular antigenic peptide that is displayed.

Engagement of the T cell receptor induces a series of molecular events characteristic of cell activation, such as, increase in tyrosine phosphorylation, $Ca^{++}$ influx, PI turnover, synthesis of cytokines and cytokine receptors, and cell division (see, Altman et al., (1990) *Adv. Immunol.* 48:227–360. For a general discussion of how T cells recognize antigen see Grey, H. M., et al., *Scientific American* pp 56–64, (November, 1989).

In mice, Class I molecules are encoded by the K, D and Qa regions of the MHC. Class II molecules are encoded by the I-A and I-E subregions. The isolated antigens encoded by the murine I-A and I-E subregions have been shown to consist of two noncovalently bonded peptide chains: an α chain of 32–38 kd and a β chain of 26–29 kd. A third, invariant, 31 kd peptide is noncovalently associated with these two peptides, but it is not polymorphic and does not appear to be a component of the antigens on the cell surface. The α and β chains of a number of allelic variants of the I-A region have been cloned and sequenced.

The human Class I proteins have also been studied. The MHC Class I of humans on chromosome 6 has three loci, HLA-A, HLA-B, and HLA-C, the first two of which have a large number of alleles encoding alloantigens. These are found to consist of a 44 kd subunit and a 12 kd $β_2$-microglobulin subunit which is common to all antigenic specificities. Further work has resulted in a detailed picture of the 3-D structure of HLA-A2, a Class I human antigen. (Bjorkman, P. J., et al., (1987) *Nature* 329:506–512). In this picture, the $β_2$-microglobulin protein and $α_3$ domain of the heavy chain are associated. The $α_1$ and $α_2$ domains of the heavy chain comprise the hypervariable region which forms the antigen-binding sites to which the peptide is bound.

Human Class II (encoded by alleles at the HLA-DR, DP, and DQ loci) glycoproteins have a domain structure, including antigen binding sites, similar to that of Class I. The Class II molecules comprise two chains, the α and β chains, which extend from the membrane bilayer. As with the Class I molecules, each subunit in Class II molecules consist of globular domains, referred to as α1, α2, β1, and β2. All except the α1 domain are stabilized by intrachain disulfide bonds typical of molecules in the immunoglobulin superfamily. The N-terminal portions of the α and β chains, the α1 and β1 domains, contain hypervariable regions which are thought to comprise the majority of the antigen-binding sites (see, Brown et al., *Nature* 364:33–39 (1993)).

As noted above, each MHC allele encodes proteins which comprise hypervariable regions and antigen binding sites specific for particular sets of antigenic peptides. If the peptides bound by the MHC molecule are from an autoantigen, allergen or other protein associated with a deleterious immune response, the hypervariable region of the MHC molecule can be used to produce immunogenic polypeptides which will elicit an immune response against the MHC molecule. These polypeptides are therefore useful in targeting particular gene products associated with deleterious immune responses because the immune response against the MHC molecule will inhibit antigen presentation associated with the deleterious immune response.

Thus, immunization with the polypeptides will be haplotype specific and result only in the inhibition of the immune response mediated by the target molecules, while leaving other alleles unaffected. Most individuals are heterozygous at each MHC locus, e.g., the HLA-DR locus. Therefore, haplotype specific therapy of disease by immunization with polypeptides of the disease susceptibility gene products of MHC genes offers a novel means of immunotherapy. This therapy is unlikely to bring about global immunosuppression since other alleles at the particular locus will be unaffected.

Polypeptides suitable for use in the present invention can be obtained in a variety of ways. Conveniently, they can be synthesized by conventional techniques employing automatic synthesizers, such as the Beckman, Applied Biosystems, or other commonly available peptide synthesizers using well known protocols. They can also be synthesized manually using techniques well known in the art. See, e.g. Stewart and Young, *Solid Phase Peptide Synthesis*, (Rockford, Ill., Pierce), 2d Ed. (1984), which is incorporated herein by reference.

Alternatively, DNA sequences which encode the particular MHC polypeptide may be cloned and expressed to provide the peptide. Cells comprising a variety of MHC genes are readily available, for instance, they may be obtained from the American Type Culture Collection ("Catalogue of Cell Lines and Hybridomas," 6th edition (1988) Rockville, Md., U.S.A. Standard techniques can be used to screen cDNA libraries to identify sequences encoding the desired sequences (see, Sambrook et al., *Molecular Cloning—A Laboratory Manual*, Cold Spring Harbor Laboratory, Cold Spring Harbor, N.Y., 1989, which is incorporated herein by reference). Fusion proteins (those consisting of all or part of the amino acid sequences of two or more proteins) can be recombinantly produced. In addition, using in vitro mutagenesis techniques, unrelated proteins can be mutated to comprise the appropriate sequences.

MHC glycoproteins from a variety of natural sources are also conveniently isolated using standard protein purification techniques. Peptides can be purified by any of a variety of known techniques, including, for example, reverse phase high-performance liquid chromatography (HPLC), ion-exchange or immunoaffinity chromatography, separation be size, or electrophoresis (See, generally, Scopes, R., *Protein Purification*, Springer-Verlag, N.Y. (1982), which is incorporated herein by reference).

It will be understood that the immunogenic MHC polypeptides of the present invention may be modified to provide a variety of desired attributes, e.g., improved pharmacological characteristics, while increasing or at least retaining substantially all of the biological activity of the unmodified peptide. For instance, the peptides can be modified by extending, decreasing the amino acid sequence of the peptide. Substitutions with different amino acids or amino acid mimetics can also be made.

The individual residues of the immunogenic MHC polypeptides can be incorporated in the peptide by a peptide bond or peptide bond mimetic. A peptide bond mimetic of the invention includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, Peptides and Proteins*, Vol. VII (Weinstein ed., 1983). Several peptide backbone modifications are known, these include, $\psi[CH_2S]$, $\psi[CH_2NH]$, $\psi[CSNH_2]$, $\psi[NHCO]$, $\psi[COCH_2]$ and $\psi[(E)$ or $(Z)$ $CH=CH]$. The nomenclature used above, follows that suggested by Spatola, above. In this context, $\psi$ indicates the absence of an amide bond. The structure that replaces the amide group is specified within the brackets.

Amino acid mimetics may also be incorporated in the peptides. An "amino acid mimetic" as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to illicit an immune response against the appropriate MHC molecule. Amino acid mimetics may include non-protein amino acids, such as β-γ-δ-amino acids, β-γ-δ-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) *Ann. Repts. Med. Chem.* 24:243–252.

As noted above, the peptides employed in the subject invention need not be identical, but may be substantially identical, to the corresponding sequence of the target MHC molecule. Therefore, the peptides may be subject to various changes, such as insertions, deletions, and substitutions, either conservative or non-conservative, where such changes might provide for certain advantages in their use. The polypeptides of the invention can be modified in a number of ways so long as they comprise a sequence substantially identical (as defined below) to a sequence in the target region of the MHC molecule.

Alignment and comparison of relatively short amino acid sequences (less than about 30 residues) is typically straightforward. Comparison of longer sequences may require more sophisticated methods to achieve optimal alignment of two sequences. Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (*USA*) 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected.

The term "sequence identity" means that two polynucleotide sequences are identical (i.e., on a nucleotide-by-nucleotide basis) over a window of comparison. The term "percentage of sequence identity" is calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The polypeptides of the invention typically comprise at least about 10 residues and more preferably at least about 18 residues. In certain embodiments the peptides will not exceed about 50 residues and typically will not exceed about 20 residues. In other embodiments, the entire subunit ($\alpha$ or $\beta$ chain) or large portions of the molecules are used. For instance, the polypeptides can comprise an extracellular domain from an MHC subunit (about 90–100 residues). Typically, the N-terminal domain ($\beta1$ or $\alpha_1$) is used. The entire extracellular region (e.g., $\beta1$ and $\beta2$ or $\alpha1$ and $\alpha2$ of class II molecules or $\alpha1$, $\alpha2$ and $\alpha3$ of class I molecules) from the subunit can also be used. Thus, a wide range of polypeptide sizes may be used in the present invention.

Since the polypeptides of the invention are typically derived from self proteins, i.e., MHC molecules involved in presenting antigens associated with immune pathologies, host immune response against the polypeptides of the invention may vary. It has been shown, however, that synthetic peptides of MHC Class I molecules can induce a specific cytotoxic T cell response (Maryanski et al., Nature 324:578 (1986)).

It is known that self peptides are continuously processed and presented by antigen presenting cells in the context of self-MHC molecules. In most instances, responses to these proteins are restricted to a limited number of epitopes. T cell selection is the consequence of the interaction of the self MHC-peptide complexes and developing T cells in the thymus. Although deletion of T cells reactive with self proteins occurs, it is not absolute and some reactivity to self peptides remains. The mechanisms by which T cells recognizing self proteins remains is unclear. Without wishing to be bound by theory, one possible explanation is that since processing of proteins is a prerequisite for T cell activation, not all combinations of peptides are presented during normal antigen processing. Those determinants not presented to T cells are referred to here as "cryptic".

The results presented below show that polypeptides of the invention derived from self MHC molecules do induce antibodies against self MHC molecules. It is thus conceivable that these polypeptides do not have natural counterparts in antigen presenting cells in vivo. Thus, polypeptides derived from self MHC molecules which comprise such cryptic determinants of whole molecules are likely to remain immunogenic while the parent molecules may be tolerated by the immune system.

Selection of MHC Molecules for Therapy

In order to select the MHC molecules for producing peptides of the invention, particular MHC molecules which are involved in the presentation of the antigen are identified.

In the case of allergies, specific allergic responses are correlated with specific MHC types. For instance, allergic reactions to ragweed are known to be associated with DR2 alleles. Marsh et al., (1989) Cold Spring Harb Symp Quant Biol 54:459–70, which is incorporated herein by reference.

Specific autoimmune dysfunctions are also correlated with specific MHC types. A list of the DQ/DR haplotypes in humans and their associations with autoimmune diseases are shown in FIG. 1. Methods for identifying which alleles, and subsequently which MHC encoded polypeptides, are associated with an autoimmune disease are known in the art. Suitable methods are described, for instance, in EP publication No. 286447, which is incorporated herein by reference. In this method several steps are followed.

First, the association between an MHC antigen and the autoimmune disease is determined based upon genetic studies. The methods for carrying out these studies are known to those skilled in the art, and information on all known HLA disease associations in humans is maintained in the HLA and Disease Registry in Copenhagen. The locus encoding the polypeptide associated with the disease is the one that would bear the strongest association with the disease.

Second, specific alleles encoding the disease associated with MHC antigen are identified. In the identification of the alleles, it is assumed that the susceptibility allele is dominant. Identification of the allele is accomplished by determining the strong positive association of a specific subtype with the disease. This may be accomplished in a number of ways, all of which are known to those skilled in the art. E.g., subtyping may be accomplished by mixed lymphocyte response (MLR) typing and by primed lymphocyte testing (PLT). Both methods are described in Weir and Blackwell, eds., Handbook of Experimental Immunology, which is incorporated herein by reference. It may also be accomplished by analyzing DNA restriction fragment length polymorphism (RFLP) using DNA probes that are specific for the MHC locus being examined. Methods for preparing probes for the MHC loci are known to those skilled in the art. See, e.g., Gregersen et al. (1986), Proc. Natl. Acad. Sci. USA 79:5966, which is incorporated herein by reference.

The most complete identification of subtypes conferring disease susceptibility is accomplished by sequencing of genomic DNA of the locus, or cDNA to mRNA encoded within the locus. The DNA which is sequenced includes the section encoding the hypervariable regions of the MHC encoded polypeptide. Techniques for identifying specifically desired DNA with a probe, for amplification of the desired region are known in the art, and include, for example, the polymerase chain reaction (PCR) technique.

As an example, over 90% of rheumatoid arthritis patients have a haplotype of DR4(Dw4), DR4(Dw14) or DR1 (See FIG. 1).

Model Systems for In vivo Testing

The following are model systems for autoimmune diseases which can be used to evaluate the effects of the immunogenic peptides of the invention on these conditions.

Systemic Lupus Erythematosus (SLE)

$F_1$ hybrids of autoimmune New Zealand black (NZB) mice and the phenotypically normal New Zealand White (NZW) mouse strain develop severe systemic autoimmune disease, more fulminant than that found in the parental NZB strain. These mice manifest several immune abnormalities, including antibodies to nuclear antigens and subsequent development of a fatal, immune complex-mediated glomerulonephritis with female predominance, remarkably similar to SLE in humans. Knight, et al., (1978) *J. Exp. Med.* 147:1653, which is incorporated hereby by reference.

In both the human and murine forms of the disease, a strong association with MHC gene products has been reported. HLA-DR2 and HLA-DR3 individuals are at a higher risk than the general population to develop SLE (Reinertsen, et al., (1970) *N. Engl. J. Med* 299:515), while in NZB/W $F_1$ mice ($H-2^{d/u}$), a gene linked to the h-$2^u$ haplotype derived from the NZW parent contributes to the development of the lupus-like nephritis.

The effect of the immunogenic peptides of the invention can be measured by survival rates and by the progress of development of the symptoms, such as proteinuria and appearance of anti-DNA antibodies.

Myasthenia Gravis (MG)

Myasthenia gravis is one of several human autoimmune diseases linked to HLA-D. McDevitt, et al., *Arth. Rheum.* (1977) 20:59 which is incorporated herein by reference. In MG, antibodies to the acetyl choline receptors (AcChoR) impair neuromuscular transmission by mediating loss of AcChoR in the postsynaptic membrane.

SJL/J female mice are a model system for human MG. In these animals, experimental autoimmune myasthenia gravis (EAMG) is induced by immunizing the mice with soluble AcChoR protein from another species. Susceptibility to EAMG is linked in part to the MHC and has been mapped to the region within H-2. Christadoss, et al., (1979) *J. Immunol.* 123:2540.

AcChoR protein is purified from *Torpedo californica* and assayed according to the method of Waldor, et al., (1983) *Proc. Natl. Acad. Sci.* 80:2713, incorporated by reference. Emulsified AcChoR, 15 ug in complete Freund adjuvant, is injected intradermally among six sites on the back, the hind foot pads, and the base of the tail. Animals are re-immunized with this same regimen 4 weeks later.

Evaluation can be made by measurement of anti-AcChoR antibodies, Anti-AcChoR antibody levels are measured by a microliter ELISA assay as described in Waldor, et al., above. The standard reagent volume is 50 ul per well. Reagents are usually incubated in the wells for 2 hr at RT. Five ug of AcChoR diluted in bicarbonate buffer, pH 9.6, is added to each well. After incubation with AcChoR, the plates are rinsed four times with a wash solution consisting of phosphate-buffer saline containing 0.05% Tween and 0.05% $NaN_3$. Mouse sera are diluted in 0.01M PBS (pH 7.2), 1.5 mM $MgCl_2$, 2.0 mM 2-mercaptoethanol, 0.05% Tween-80, 0.05% $NaN_3$ (P-Tween buffer) and incubated on the plate. After the plate is washed, β-galactosidase-conjugated sheep anti-mouse antibody diluted in P-Tween buffer is added to each well. After a final washing, the enzyme substrate, p-nitrophenyl-galctopyranoside is added to the plate, and the degree of substrate catalysis is determined from the absorbance at 405 nm after 1 hr.

Anti-AcChoR antibodies are expected to be present in the immunized with AcChoR mice as compared to nonimmunized mice. Treatment with immunogenic peptides is expected to significantly reduce the titer of anti-AcChoR antibodies in the immunized mice.

The effect of treatment with the immunogenic peptides on clinical EAMG can also be assessed. Myasthenia symptoms include a characteristic hunched posture with drooping of the head and neck, exaggerated arching of the back, splayed limbs, abnormal walking, and difficulty in righting. Mild symptoms are present after a standard stress test, and should be ameliorated by administration of immunogenic peptides after a period of time after which antibody titer has fallen.

Rheumatoid Arthritis (RA)

In humans, susceptibility to rheumatoid arthritis is associated with HLA D/DR. The immune response in mice to native type II collagen has been used to establish an experimental model for arthritis with a number of histological and pathological features resembling human RA. Susceptibility to collagen-induced arthritis (CIA) in mice has been mapped to the H-2 I region, particularly the I-A subregion. Huse, et al., (1984) *Fed. Proc.* 43:1820.

Mice from a susceptible strain, DBA-1 are caused to have CIA by treatment of the mice with native type II collagen, using the technique described in Wooley and Luthra, (1985) *J. Immunol.* 134:2366, incorporated herein by reference.

In another model, adjuvant arthritis in rats is an experimental model for human arthritis, and a prototype of autoimmune arthritis triggered by bacterial antigens, Holoschitz, et al., *Prospects of Immunology* (CRC Press) (1986); Pearson *Arthritis Rheum.* (1964) 7:80. The disease is the result of a cell-mediated immune response, as evidenced by its transmissibility by a clone of T cells which were reactive against the adjuvant (MT); the target self-antigen in the disease, based upon studies with the same cloned cells, appears to be part(s) of a proteoglycan molecule of cartilage.

Adjuvant disease in rats is produced as described by Pearson, i.e., by a single injection of Freund's adjuvant (killed tubercle bacilli or chemical fractions of it, mineral oil, and an emulsifying agent) given into several depot sites, preferably intracutaneously or into a paw or the base of the tail. The adjuvant is given in the absence of other antigens.

The effect of immunogenic peptide treatment of manifestations of the disease are monitored. These manifestations are histopathological, and include an acute and subacute synovitis with proliferation of synovial lining cells, predominantly a mononuclear infiltration of the articular and particular tissues, the invasion of bone and articular cartilage by connective tissue pannus, and periosteal new bone formation, especially adjacent to affected joints. In severe or chronic cases, destructive changes occur, as do fibrous or bony ankylosis. These histopathological symptoms are expected to appear in control animals at about 12 days after sensitization to the Freund's adjuvant.

Insulin Dependent Diabetes Mellitus (IDDM)

IDDM is observed as a consequence of the selective destruction of insulin-secreting cells within the Islets of Langerhans of the pancreas. Involvement of the immune system in this disease is suggested by morphologic evidence of early infiltration of the Islets by mononuclear cells, by the detection of anti-islet cell antibodies, by the high frequency of HLA-DR3 and -DR4 alleles in IDDM populations, and by clinical associations between IDDM and various autoimmune diseases. An animal model for spontaneous IDDM and thyroiditis has been developed in the BB rat. As in humans, the rat disease is controlled in part by the genes encoding the MHC antigens, is characterized by islet infiltration, and is associated with the presence of anti-islet antibodies. The I-E equivalent Class II MHC antigens appear to be involved in manifestation of the autoimmune diseases in the BB rat. Biotard, et al., *Proc. Natl. Acad. Sci. USA* (1985) 82:6627.

In morphologic evaluation, insulitis is characterized by the presence of mononuclear inflammatory cells within the islets. Thyroiditis is characterized by focal interstitial lymphocytic infiltrate within the thyroid gland, as a minimum criterion. Most severe cases show diffuse extensive lymphocytic infiltrates, disruption of acini, fibrosis, and focal Hurthle call change. See Biotard et al.

Treatment of the BB rats with immunogenic peptides of the invention is expected to ameliorate or prevent the manifestation of the clinical and morphological symptoms associated with IDDM and thyroiditis.

In another spontaneous model, the NOD mouse strain (H-2K$^d$D$^b$) is a murine model for autoimmune IDDM. The disease in these animals is characterized by anti-islet cell antibodies, severe insulitis, and evidence for autoimmune destruction of the β-cells. Kanazawa, et al., *Diabetologia* (1984) 27:113. The disease can be passively transferred with lymphocytes and prevented by treatment with cyclosporin-A (Ikehara, et al., *Proc. Natl. Acad. Sci. USA* (1985) 82:7743; Mori, et al.), *Diabetologia* (1986) 29:244. Untreated animals develop profound glucose intolerance and ketosis and succumb within weeks of the onset of the disease. Seventy to ninety percent of female and 20–30% of male animals develop diabetes within the first six months of life. Breeding studies have defined at least two genetic loci responsible for disease susceptibility, one of which maps to the MHC. Characterization of NOD Class II antigens at both the serologic and molecular level suggest that the susceptibility to autoimmune disease is linked to I-Aβ. Acha-Orbea and McDevitt, *Proc. Natl. Acad. Sci. USA* (1970) 84:235.

Treatment of Female NOD mice with immunogenic peptides is expected to lengthen the time before the onset of diabetes and/or to ameliorate or prevent the disease.

Experimental Allergic Encephalomyelitis (EAE)

Experimental allergic encephalomyelitis (EAE) is an induced autoimmune disease of the central nervous system which mimics in many respects the human disease of multiple sclerosis (MS). The disease can be induced in many species, including mice and rats.

The disease is characterized by the acute onset of paralysis. Perivascular infiltration by mononuclear cells in the CNS is observed in both mice and rats. Methods of inducing the disease, as well as symptomology, are reviewed in Aranson (1985) in *The Autoimmune Diseases* (eds. Rose and Mackay, Academic Press, Inc.) pp. 399–427, and in Acha-Orbea et al. (1989), *Ann. Rev. Imm.* 7:377–405.

One of the genes mediating susceptibility is localized in the MHC class II region (Moore et al. (1980), *J. Immunol.* 124:1815–1820). The best analyzed encephalitogenic protein is myelin basic protein (MBP), but other encephalitogenic antigens are found in the brain. The immunogenic epitopes have been mapped (see Acha-Orbea et al., supra.). In the PL mouse strains (H-2u) two encephalitogenic peptides in MBP have been characterized: MBP peptide p35-47 (MBP 35-47), and acetylated (MBP 1-9). In humans, preferred autoantigenic peptides for treatment of MS comprise amino aids 84-102 and 148-162 of MBP.

The effect of the immunogenic peptides of the invention on ameliorating and preventing disease symptoms in individuals in which EAE has been induced can be measured by survival rates, and by the progress of the development of symptoms. An example of the use of immunogenic peptides in the treatment of EAE is provided below.

Formulation and Administration

The peptides of the present invention and pharmaceutical compositions thereof are useful for administration to mammals, particularly humans, to treat and/or prevent deleterious immune responses. Suitable formulations are found in *Remington's Pharmaceutical Sciences,* Mack Publishing Company, Philadelphia, Pa., 17th ed. (1985), which is incorporated herein by reference.

The immunogenic peptides of the invention are administered prophylactically or to an individual already suffering from the disease. The compositions are administered to a patient in an amount sufficient to elicit an effective immune response to the MHC molecule from which the peptides are derived. An amount adequate to accomplish this is defined as "therapeutically effective dose" or "immunogenically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 0.1 mg to about 1.0 mg per 70 kilogram patient, more commonly from about 0.5 mg to about 0.75 mg per 70 kg of body weight. Boosting dosages are typically from about 0.1 mg to about 0.5 mg of peptide using a boosting regimen over weeks to months depending upon the patient's response and condition. A suitable protocol would include injection at time 0, 2, 6, 10 and 14 weeks, followed by booster injections at 24 and 28 weeks.

It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

For therapeutic use, administration should begin at the first sign of autoimmune or allergic disease. This is followed by boosting doses until at least symptoms are substantially abated and for a period thereafter. In some circumstances, loading doses followed by boosting doses may be required. The resulting immune response helps to cure or at least partially arrest, symptoms and/or complications. Vaccine compositions containing the peptides are administered prophylactically to a patient susceptible to or otherwise at risk of the disease to elicit an immune response against the target MHC antigen.

The pharmaceutical compositions are intended for parenteral or oral administration. Preferably, the pharmaceutical compositions are administered parenterally, e.g., subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

As noted above, the compositions are intended to induce an immune response to the peptides. Thus, compositions and methods of administration suitable for maximizing the immune response are preferred. For instance, peptides may be introduced into a host, including humans, linked to a carrier or as a homopolymer or heteropolymer of active peptide units. Alternatively, the a "cocktail" of polypeptides can be used. A mixture of more than one polypeptide has the advantage of increased immunological reaction and, where different peptides are used to make up the polymer, the additional ability to induce antibodies to a number of epitopes. For instance, polypeptides comprising sequences from hypervariable regions of α and β chains may be used in combination. Useful carriers are well known in the art, and include, e.g., thyroglobulin, albumins such as human serum albumin, tetanus toxoid, polyamino acids such as poly(lysine:glutamic acid), influenza, hepatitis B virus core protein, hepatitis B virus recombinant vaccine and the like.

The use of more than one polypeptide is particularly useful to enhance the immune response against polypeptides of the invention. As demonstrated below, although the polypeptides may be derived from self MHC molecules expressed in the patient, they can induce an immune response. In some instances, the immune response to the self polypeptide may not be sufficiently strong. In these instances, it may be necessary to break tolerance to the polypeptide. The compositions may comprise one or more of the foreign polypeptides that are sufficiently similar to the self polypeptides to induce an immune response against both the foreign and self polypeptides (see, Mamula et al. *J. Immunol.* 149:789–795 (1992). Suitable proteins include synthetic polypeptides designed for this purpose or polypeptide sequences from homologous proteins from natural sources, such as proteins encoded by a different allele at the same locus as the self polypeptide.

The compositions also include an adjuvant. A number of adjuvants are well known to one skilled in the art. Suitable adjuvants include incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic peptide.

A particularly useful adjuvant and immunization schedule are described in Kwak et al. *New Eng. J. Med.* 327-1209–1215 (1992), which is incorporated herein by reference. The immunological adjuvant described there comprises 5% (wt/vol) squalene, 2.5% Pluronic L121 polymer and 0.2% polysorbate in phosphate buffered saline.

The concentration of immunogenic peptides of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

The peptides of the invention can also be expressed by attenuated viral hosts, such as vaccinia or fowlpox. This approach involves the use of vaccinia virus as a vector to express nucleotide sequences that encode the peptides of the invention. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848, incorporated herein by reference. Another vector is BCG (Bacille Calmette Guerin). BCG vectors are described in Stover et al. (*Nature* 351:456–460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

The peptides can also be used for diagnostic purposes. For instance, they can be used to screen for autoantibodies to ensure that the vaccination has been effective.

The following examples are offered by way of illustration, not by way of limitation.

EXAMPLE 1

This example shows that immunization of mice with peptides of the invention elicit an immune response to the target MHC antigen.

The model system used was Experimental Autoimmune Encephalomyelitis (EAE). As explained above, EAE is an animal model of a T cell mediated autoimmune demyelinating disease that resembles human Multiple Sclerosis (MS). The disease is characterized by the development of an acute paralytic attack followed by recovery. Spontaneous remissions followed by variable recovery are seen when animals are observed over a three month period. In view of these features EAE is an ideal model for the study of immunotherapy of chronic autoimmune disease.

Like MS, susceptibility to EAE is linked to certain alleles of mouse Ia genes, with I-A$^{s,u,\&k}$ strains being susceptible while I-A$^{b\&d}$ strains relatively resistant. EAE can be prevented and the severity of CR-EAE reduced, following treatment with monoclonal anti-I-A antibody 10-3.6 (Sriram, et al. (1983) *J. Exp. Med.*, 158:1362). Monoclonal antibody 10-3.6 recognizes the serological specificity Ia17, on the β chain of I-A molecule, binding to residues 63–67 of the β chain of the alleles of IA$^{s,u,f,r}$ and $^{k11}$.

Synthetic peptides that spanned the monoclonal antibody 10-3.6 binding site on the β chain of I-A$^s$ were generated. These peptides were I-A$^{sβ}$ p18mer, spanning residues 58–75 (SEQ ID NO: 1) and I-A$^{sβ}$p10mer spanning residues 60–70 (SEQ ID NO: 2) of the third hypervariable region of the β chain (FIG. 2). The peptides were obtained from (Macromolecular Resources, Colorado State Univ, Fort Collins Colo.).

Figure 3A:
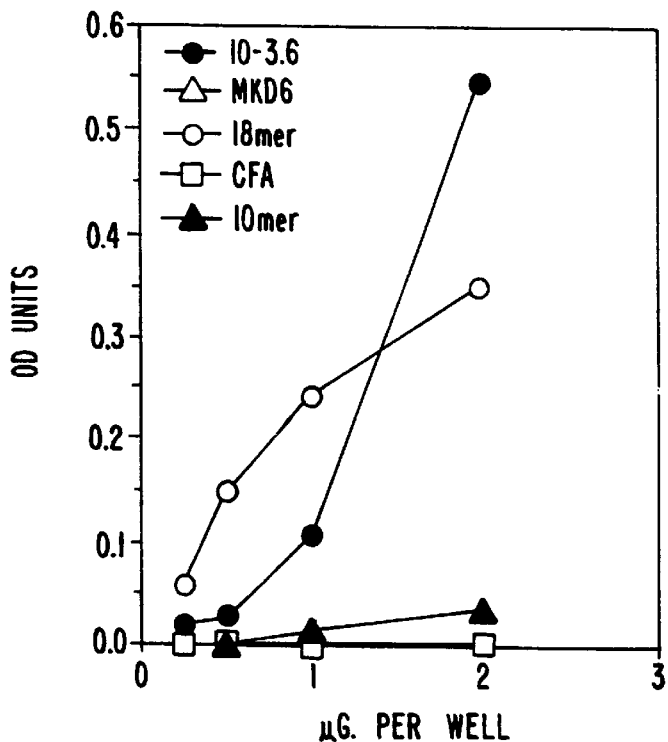
FIG. 3A shows the results of ELISA binding assays of antibodies obtained from animals immunized with the 18mer peptide.
Figure 3B:
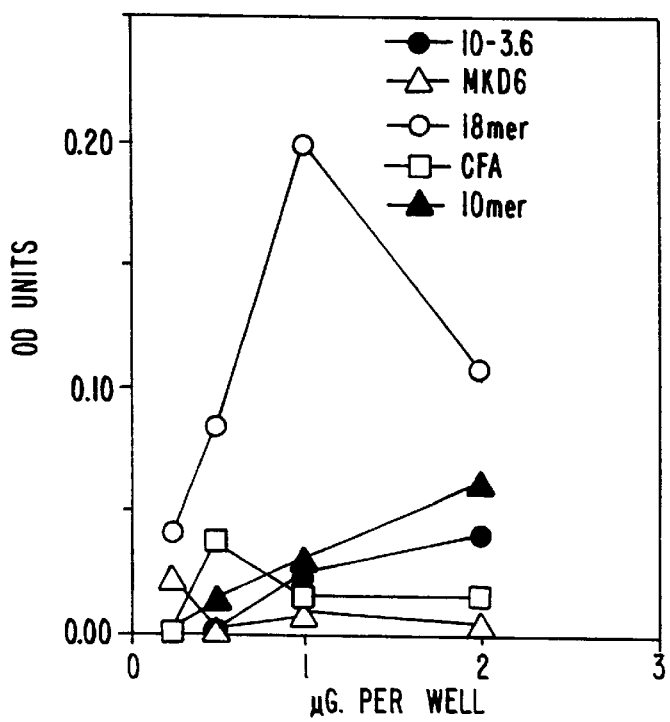

The results of ELISA binding assays of antibodies obtained from animals immunized with the 18mer and the 10mer are shown in FIGS. 3A and 3B, respectively. Five female SJL mice, 8 weeks of age (obtained from NIH, Bethesda, Md.) were immunized on the dorsum with 350 μg of the peptide in complete Freund's Adjuvant containing 50 μg of H37RA (CFA). The animals were re-immunized with 200 μg of the peptide 7 days later and bled via tail vein 3 weeks after the second immunization. Control animals were immunized with CFA alone or with an irrelevant 20mer peptide (pb 57, a 20mer peptide of thrombin, gift of W. Church, University of Vermont, Burlington Vt.). The sera were pooled from five animals and the immunoglobulins were precipitated with supersaturated ammonium sulphate according to standard procedures. Solubilized precipitate was further purified by chromatography over a QAE column and quantified by absorbance reading 280 nm on a spectrophotometer.

ELISA assays were performed by coating ELISA plates (Corning, N.Y.) with antigen (2 μg/ well 10-mer peptide or with 1 μg/well of the 18-mer peptide) in 100 μl of bicarbonate buffer (pH9.2) overnight. The wells were washed in ELISA washing buffer (PBS with 0.05% Tween 20), unoccupied sites blocked with 1% bovine serum albumin (Sigma, St. Louis, Mo.) in PBS for 30 minutes and washed. 2 μg, 1 μg, 0.5 μg and 0.25 μg of antibody diluted in ELISA buffer was added to each well. After 45 minutes the wells were washed and alkaline phosphatase-conjugated goat-anti-mouse lgG (Tago, Millbrae, Calif.) was added at a dilution of 1:5000. After 30 minutes the wells were washed and 100 μl of the substrate (5 mgs of p-nitrophenyl phosphate dissolved in 10% diethanolamine (Sigma) to a final concentration of 1 mg/m) was added to the wells. The color reaction was read in a Bio-Tek ELIZA reader (Winooski, Vt.) at 405 nm at 120 minutes. Results are expressed as mean absorbance of triplicate wells read at 405 nm. after subtraction of background absorbance at 405 nm units (Absorbance 405 nm in wells to which no primary antibody was added).

Antibodies to the 18mer antigen were detected in SJL mice following immunization with the I-A$^s$β p18mer peptide (FIG. 3A). The 10mer peptide was poorly immunogenic and did not result in the development of a significant antibody titre (FIG. 3B). Also, monoclonal antibody 10-3.6 bound to the 18mer peptide as expected, while the control isotype-matched antibody MKD6 (which recognizes a polymorphic region of I-A$^d$) showed no binding. Only the anti 18mer antisera bound to the 10mer peptide suggesting that the anti-18mer antibody recognized a region distinct from that recognized by antibody 10-3.6. Neither peptide gave rise to a proliferative T cell response. Immunization with an irrelevant 20mer peptide (pb 57, a synthetic peptide of thrombin protein) did not elicit antibodies to either the 20mer or the 10mer peptide (data not shown).

To determine if the serum antibody was specific to IA molecules, an ELISA assay using soluble I-A molecules as the ligand was used.

Soluble l-A$^s$ protein was prepared as previously described in Sharma et al. (1991) *Proc. Natl. Acad. Sci. USA* 88:11465. Soluble DR was prepared from homozygous typing cell line GMO-3107, that is homozygous for HLA-DR2. Briefly, the DR2 typing cell line was grown in 8 liter culture flasks and at cell density of 1×10$^6$ cells/ml, the cells were then harvested and a detergent lysate of the membrane preparation was passed over a column containing anti-DR antibody (L234) coupled to sepharose 4B. The bound DR molecules were eluted at pH 11.3 and the protein peaks pooled. A 12% SDS-PAGE gel was run to establish the purity of the preparation. The soluble l-A$^s$ and DR proteins were diluted in bicarbonate buffer pH9.2. 1 μg of the protein in 100 μl of buffer was added to the well and the ELISA assay was performed as described above.

Figure 4A:
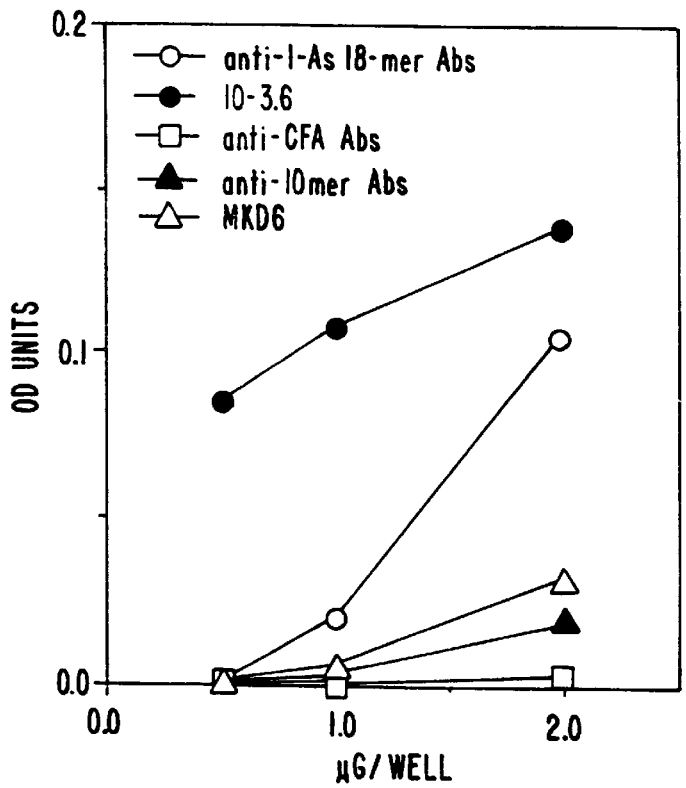
FIG. 4A shows the results of ELISA binding assays of antibodies to soluble I-A$^s$.
Figure 4B:
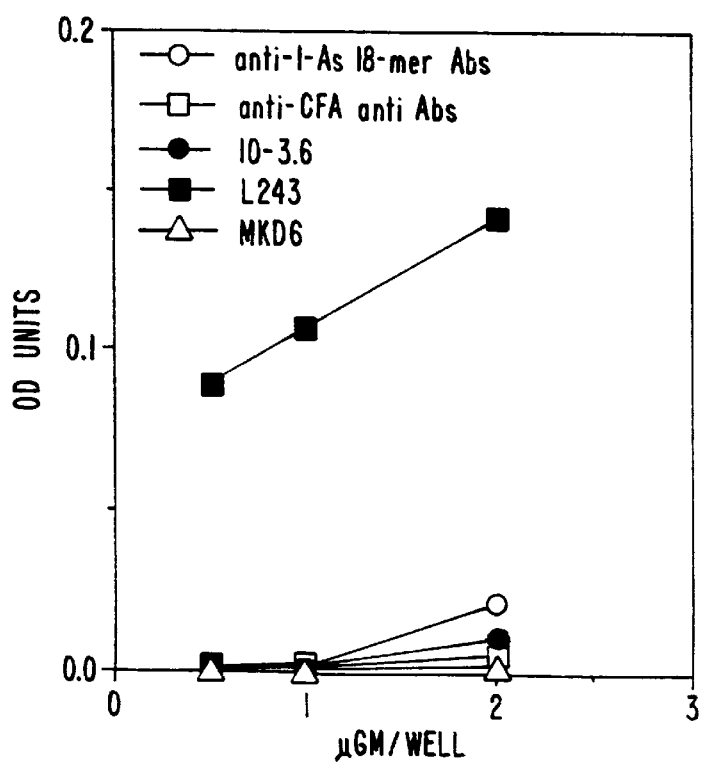
FIG. 4B shows the results of ELISA binding assays of antibodies to soluble DR.
Figure 5A:
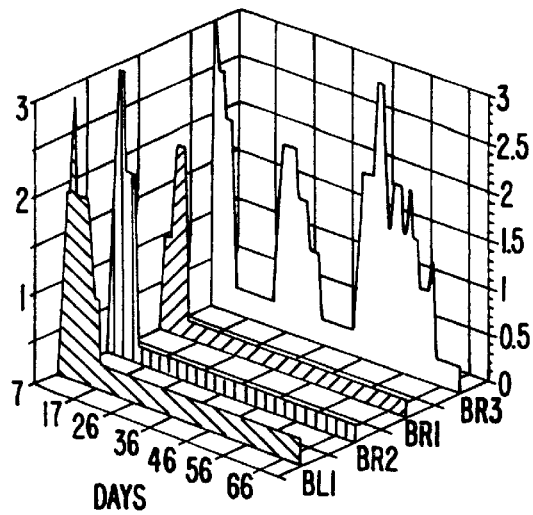
FIGS. 5A and 5C shows the clinical course of CR-EAE in SJL/J mice that received the 18mer peptide in CFA.
Figure 5B:
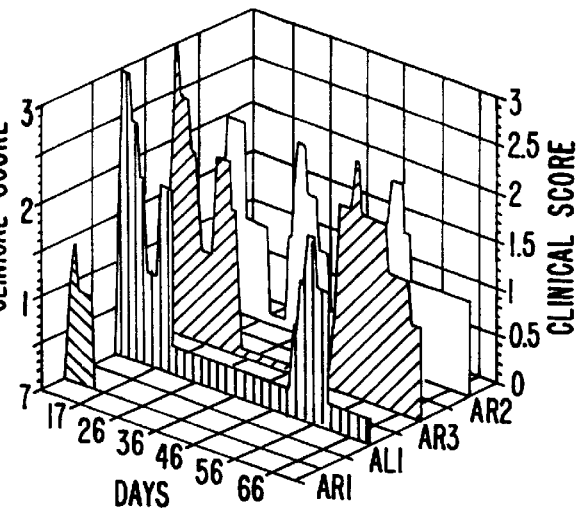
FIGS. 5B and 5D shows the clinical course of CR-EAE in SJL/J mice that received CFA alone.
Figure 5C:
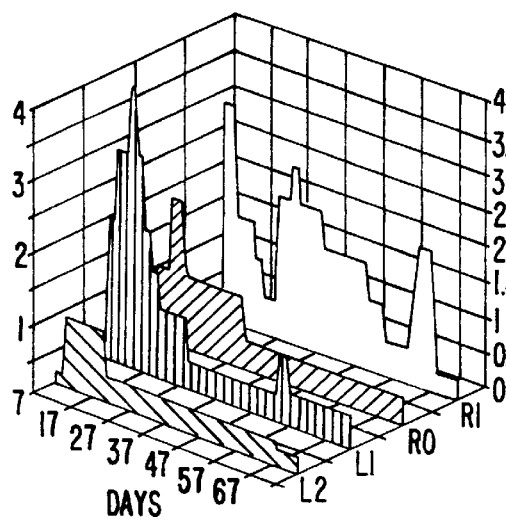
Figure 5D:
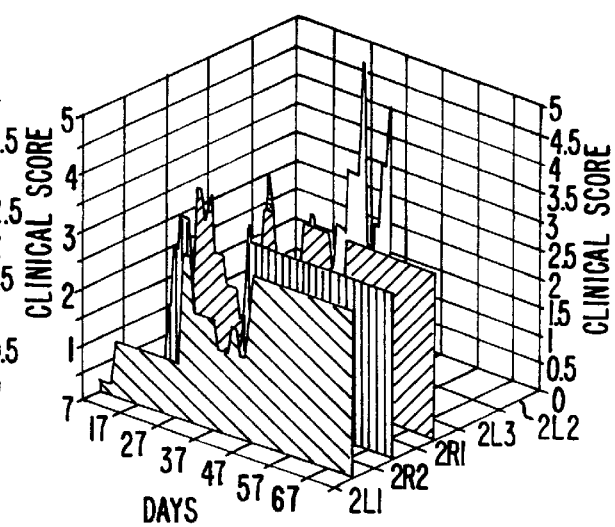

As shown in FIG. 4A, antibodies from I-A$^s$β p18mer peptide immunized animals bound to the soluble I-A$^s$ antigen. Antibodies obtained from animals that were immunized with the I-Aβ p10 mer or with CFA alone showed no binding to the soluble I-A$^s$. When soluble HLA-DR2 was used (FIG. 4B) as a control antigen, there was no binding of the anti I-Asβ 18mer or the 10-3.6 antibodies, but there was binding of anti HLA-DR antibody L243. These studies establish, that anti I-A specific antibodies can be generated in animals autologous for the I-A gene products, following immunization with I-A peptides.

EXAMPLE 2

This example shows that the induction of anti I-A$^s$ antibody response is sufficient to prevent the development of acute and CR-EAE.

Female SJL/J mice, 6–12 weeks of age were obtained from NIH (Bethesda, Md.) and maintained according to standard techniques. The mice were immunized on the back with 150 μl of an emulsion comprising either Complete Freunds Adjuvant (CFA, to which 350 μg/ml of H37RA was added, CFA with 400 μgm of I-A$^s$β p18-mer, CFA with 400 μgm of I-A$^s$β p10-mer, or CFA with 400 μgm of 57pb (20mer peptide of thrombin, irrelevant peptide).

Four weeks later all animals were challenged with 800 μgm of Mouse Spinal Cord Homogenate (MSCH) in CFA. The immunization with MSCH was repeated 7 days later and disease was monitored between days 10–20. Disease was graded as follows: (1) limp tail, (2) paralysis of one limb, (3) paralysis of two limbs, (4) moribund, (5) death. Twenty days following immunization with MSCH all animals were perfused with 4% paraformaldehyde and the brain and spinal cord obtained for histological analysis. Histology was graded as follows: 4+, greater than 6 perivascular cuffs present in 6 non-overlapping fields observed at medium power; 3+, 3–6 perivascular cuffs present in nonoverlapping fields at medium power; 2+, 1–3 perivascular cuffs present in nonoverlapping fields at medium power; 1+, meningeal infiltration only. Histology of brain including cerebellum and brain stem was studied in all animals from experiment 1.

The results of these experiments (Table 1) show that immunization with I-A$^s$β p18mer peptide protects against the development of EAE. In all, only 3 out of 16 animals (23%) that were vaccinated with the peptide I-A$^s$β p18mer developed EAE. In animals that were injected with CFA alone or CFA with p57 (an irrelevant 20mer peptide) 13 of the 16 animals (81%) developed EAE. Histological evidence of the difference in severity was also confirmed. I-A$^s$βp10mer was not successful in generating anti I-A$^s$ antibody and did not prevent EAE.

TABLE 1

Prevention Of EAE Following Immunization With I-A$^s$β Chain Peptide 58–75

| Treatment | No Animals | No Paralyzed | Mean Severity Of Mice Paralyzed | Day Of Onset | Histology |
|---|---|---|---|---|---|
| Exp. 1 | | | | | |
| CFA alone | 4 | 3 | 3.0 | 12 | 3 |
| CFA + I-A$^s$ p58–75 | 4 | 0 | 0 | 0 | — |
| Exp. 2 | | | | | |
| CFA + 57 pb | 6 | 4 | 2.4 | 13 | Not Done |
| CFA I-A$^s$ p58–75 | 6 | 1 | 3.0 | 21 | Not Done |
| Exp. 3 | | | | | |
| CFA alone | 6 | 6 | 2.4 | 13 | Not Done |
| I-A$^s$ p58–75 | 6 | 2 | 2.0 | 16 | Not Done |

TABLE 1-continued

Prevention Of EAE Following Immunization
With I-A$^s$β Chain Peptide 58–75

| Treatment | No Animals | No Paralyzed | Mean Severity Of Mice Paralyzed | Day Of Onset | Histology |
|---|---|---|---|---|---|
| Exp. 4 | | | | | |
| CFA + I-A$^s$ p60–70 (10-mer) | 6 | 6 | 3.0 | 11 | |
| CFA alone | 6 | 6 | 2.6 | 12 | |
| Total | | | | | |
| I-A$^s$ 58–75 | 16 | 3[1] | 2.0 | | |
| I-A$^s$ p60–70 | 6 | 6 | 3.0 | | |
| All Controls | 16 | 13 | 2.5 | | |

[1]X2 = I-Ap (18 mer) VS CFA alone (p < .0001)
= I-Ap (10 mer) VS CFA alone p, not significant In order to determine the effect of immunization with I-A$^s$β p18mer peptides on established disease, vaccination of animals with I-A$^s$β p18mer peptide, was initiated following recovery from the initial paralytic attack (Table 2).

SJL mice 6–8 weeks of age were immunized on days 0 and 7 with 400 μgms MBP peptide p91-103 (Multiple Peptide System, San Diego Calif.) in CFA containing 50 μgm/ml of H37RA. Fourteen days later, regional draining lymph node cells were harvested and cultured in 24 well plates (Falcon) at a concentration of 6×10$^6$ cells/well in 1.5 mls of RPMI 1640 medium containing 10% fetal bovine serum (Hyclone Labs, Logan, Utah), 2 mM L-glutamine, 5×10$^{-5}$ M 2-mercaptoethanol, 1% penicillin/streptomycin, and 5 μgm/ml of peptide or 10 μg/ml of p91-103 peptide. Following a 4 day in vitro stimulation, antigen reactive T cell blasts were harvested via ficoll-hypaque gradient centrifugation (Hypaque 1077, Sigma, St. Louis, Mo.), washed twice in PBS and injected into recipient mice (1.5×10$^7$ cells/animal in 500 ul PBS, i.p.).

Animals were observed for the development of EAE and upon recovery were immunized with either 400 μgm of I-A$^s$β 18 mer peptide in CFA (Group 1) or CFA alone (Group 2). Recovery was defined as an improvement of 2 clinical grades or more that was present for more than 48 hrs. In experiment 1, recovery occurred in all animals by day 17 and animals were injected with the I-A$^s$β 18 mer peptide or CFA on day 18 and in the second experiment, the animals were treated with the I-A$^s$β 18 mer peptide on day 24. Animals were followed daily up to day 75.

TABLE 2

Clinical course of CR-EAE in animals treated with I-A$^s$β 18 mer peptide after recovery from the initial paralytic attack Summary of two experiments

| | No. of Mice per Group | Mean day onset of paralysis | Mean severity |
|---|---|---|---|
| Initial Attack Group 1 | | | |
| I-A$^s$β 18 mer peptide treated | 8 | 8.3 | 2.2 |
| Group 2 | | | |
| CFA treated | 9 | 8.9 | 2.4 |

TABLE 2-continued

Clinical course of CR-EAE in animals treated with I-A$^s$β 18 mer peptide after recovery from the initial paralytic attack Summary of two experiments

| | No. of Mice per Group | Mean day onset of paralysis | Mean severity |
|---|---|---|---|
| First Relapse | | | |
| Group 1 | 2/8 | 27 | 1.8 |
| Group 2 | 8*/9 | 32 | 3.0 |
| Second Relapse | | | |
| Group 1 | 2/8 | 57 | 2.0 |
| Group 2 | 5/7 | 50 | 2.3 |
| Cumulative relapses | | | |
| Group 1 | 4# | | |
| Group 2 | 13 | | |

*Two animals died in the first relapse.
p < 0.05, Wilcoxan rank sum test

These studies show that overall there were only four relapses in the I-A$^s$β p18mer treated group when compared to 13 in the control group. In Experiment 2, the relapses were more severe with two deaths at the first relapse and the remaining three animals displaying Grade 2 or greater paralysis, for the remainder of the study (FIG. 5). Overall, the relapse rate (Number of relapses/number of animals) in animals that received I-A$^s$βp20mer was 0.27, while those in the control group overall was 1.3 (p<0.05).

This study establishes the efficacy of vaccination with I-A$^s$β peptides as a therapeutic strategy in the treatment of autoimmune disease. The clinical effect observed here closely parallels the results obtained with in vivo therapy with anti I-A antibody in the treatment of acute and CR-EAE.

EXAMPLE 3

This example presents the results of flow cytometric analysis, T cell proliferation assays to analyze the nature of the immune response induced by polypeptides of the invention.

The auto-anti-I-A antibodies from I-A$^s$β 18-mer peptide vaccinated animals are specific for native I-A$^s$ expressed on the cell surface.

Flow cytometric analysis was performed on splenic lymphocytes to determine whether or not the antiserum from I-A$^s$β 18-mer peptide vaccinated animals could recognize native I-A$^s$ molecule on the cell surface. Splenic lymphocytes containing T-cells, B-cells, and monocytes were obtained from SJL/J (I-A$^s$) and BALB/c (I-A$^d$) mice. The cells were then stained in vitro with purified antiserum from animals vaccinated either with I-A peptide or CFA alone. A goat anti-mouse IgG Fc conjugated to fluorescein isothyocyanate (FITC) was used as secondary antibody. Monoclonal antibody 10-3.6 conjugated to FITC was used as a positive control.

The results of these experiments indicated that 36.17% of splenic lymphocytes were stained by the I-A$^s$β 18-mer antiserum at a concentration of 50 μg/ml. This is compared to 40% of cells stained with the monoclonal anti-I-A antibody 10-3.6. In contrast only 1.91% of the cells stained with 50 μg of the CFA antiserum and 1.5% of the cells stained with anti-I-A$^d$ mAb MKD6. The anti-I-A$^s$β 18-mer antiserum was specific for the SJL/J spleen cells since only 3.78% of BALB/c spleen cells were recognized.

Figure 6A:
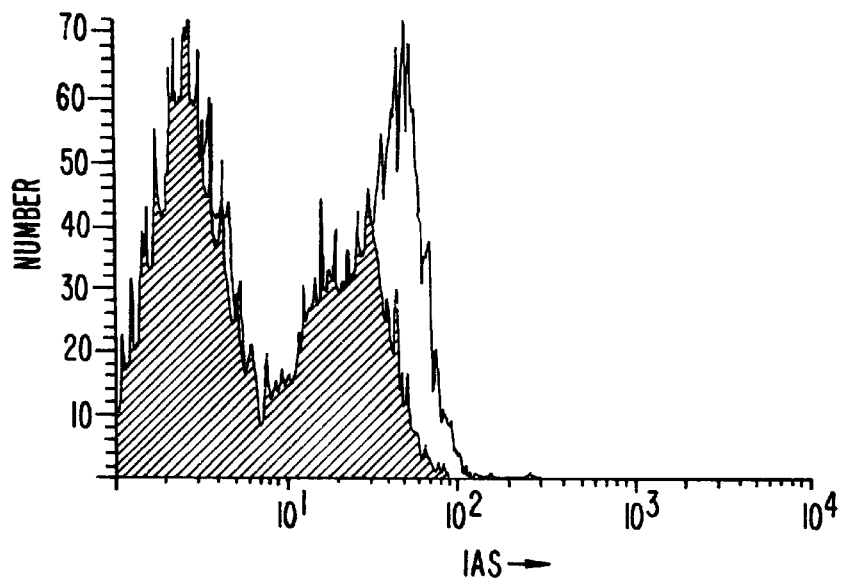
FIG. 6 shows blocking of binding of the anti-I-A$^s$ monoclonal antibody 10-3.6 by anti-I-A$^s$β 18-mer peptide antiserum. This figure is a plot of mean fluorescent intensity at various concentrations of 10-3.6-FITC.
Figure 6B:
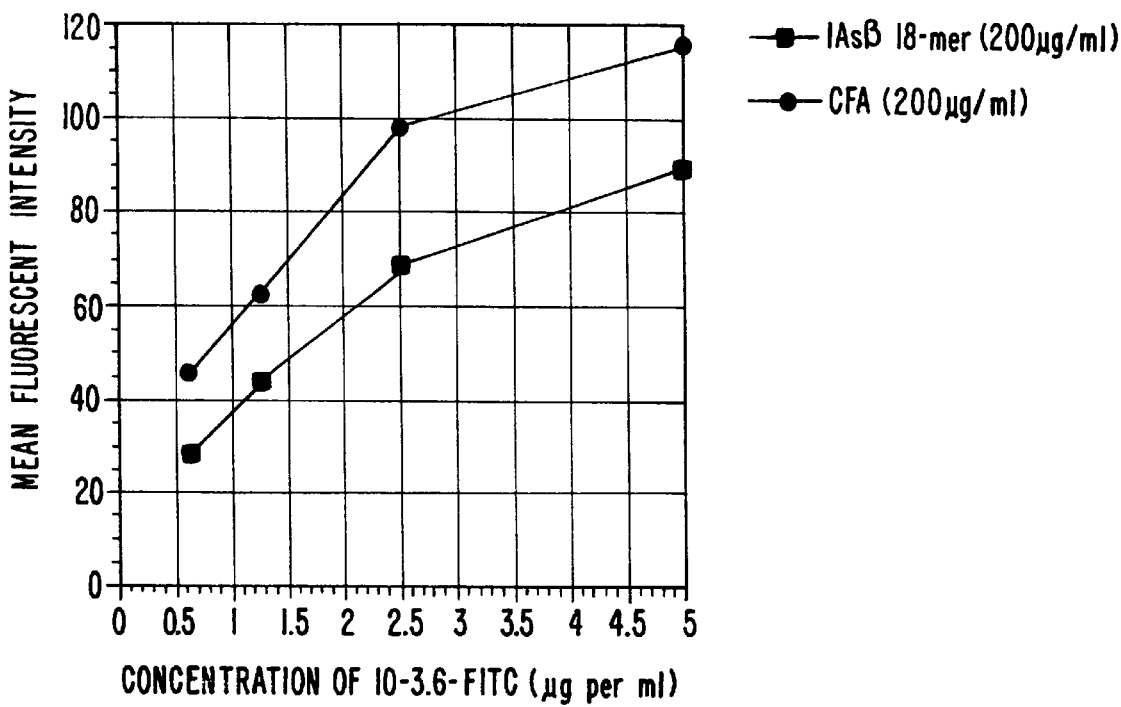

In a separate experiment, SJL spleen cells were preincubated for 1 hr. with 200 μg/ml of either the anti-I-A$^s$β 18-mer peptide antiserum or CFA control antiserum. The cells were then washed and incubated for 30 min. with FITC-conjugated 10-3.6 at concentrations of 5, 2.5, 1.25, and 0.625 µg/ml. Cells incubated with the anti-I-A$^s$β 18-mer peptide antiserum demonstrated a mean 44.4±11.6% reduction in the mean fluorescent intensity at all concentrations of 10-3.6 when compared to those samples preincubated with the control antiserum (FIG. 6).

These studies establish that following vaccination with the I-A$^s$β 18-mer peptide, anti-I-A$^s$ specific antibodies are generated in animals autologous for the I-A gene products. The auto anti-I-A antibody can inhibit Class II-restricted T-cell proliferative responses.

Figure 7:
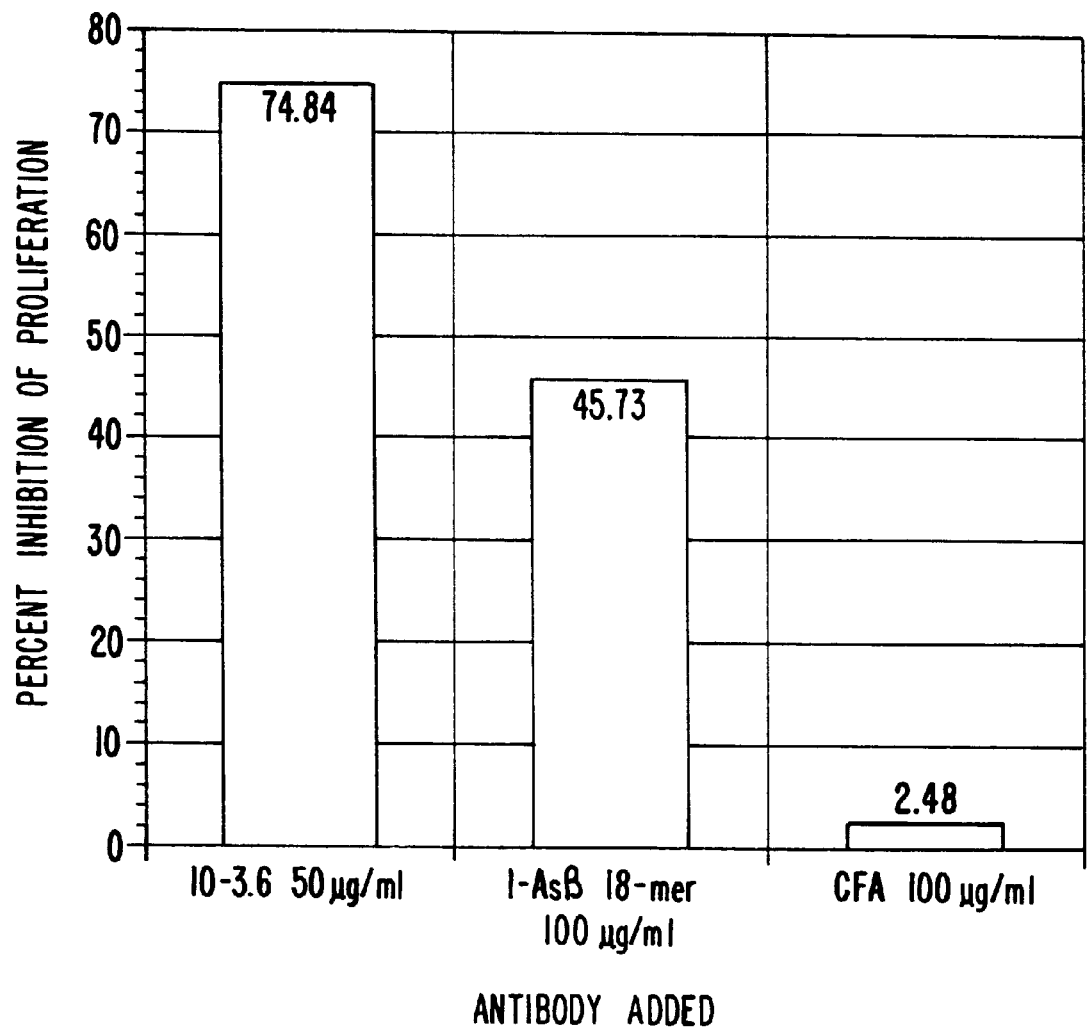
FIG. 7 shows percent inhibition of the proliferation of SJL lymph node cells to MBP p91-103 peptide by either mAb 10-3.6, anti-I-A$^s$β 18-mer peptide antiserum, or CFA control antiserum.

To determine whether the anti-I-A antibodies elicited by vaccination with I-A peptide can inhibit functional responses, a T-cell proliferative assay was performed. SJL/J mice were immunized with MBP p91-103 peptide in CFA. Nine days later the lymph nodes were removed and cultured in vitro in the presence of the p91-103 peptide. Purified antiserum from the I-A$^s$β 18-mer peptide vaccinated mice was included in the assay (100 µg/ml). Alternatively, as positive and negative controls, mAb 10-3.6 (50 µg/ml) and CFA antiserum (100 µg/ml) were included in separate sets of wells respectively. Only the anti-I-A$^s$β 18-mer antiserum and the 10-3.6 mAb were able to inhibit proliferation (43% vs. 72% inhibition). CFA antiserum had little effect (2.48%). (FIG. 7).

Animals vaccinated with I-A$^s$β 18-mer peptide fail to develop a proliferative response to MBP and PPD.

Figure 8A:
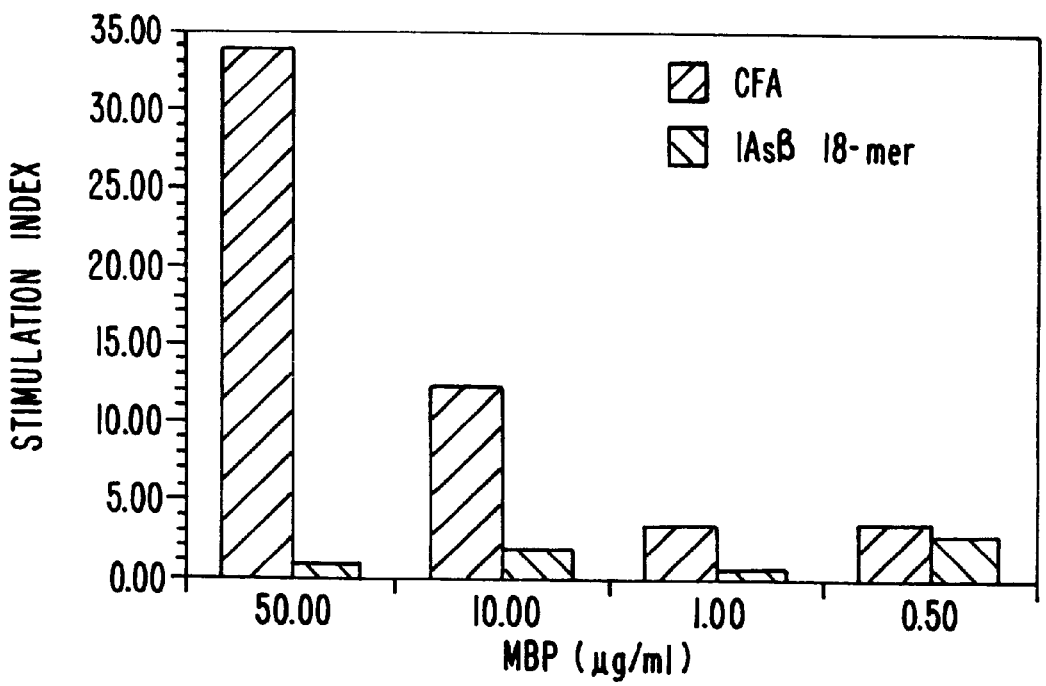
FIGS. 8A and 8B show proliferative responses of regional lymph node cells to MBP (FIG. 8A) and PPD (FIG. 8B) in SJL mice that were initially vaccinated with 400 μg of I-A$^s$β 18-mer in CFA, or CFA alone, and were then immunized with 400 μg/animal of MBP in CFA four weeks later. Results are expressed as the stimulation index: mean cpm in wells with antigen divided by the mean cpm in wells without antigen. The mean background cpm in wells without antigen in the group that received I-A$^s$β 18-mer was 374 cpm and those that received CFA alone was 399 cpm.
Figure 8B:
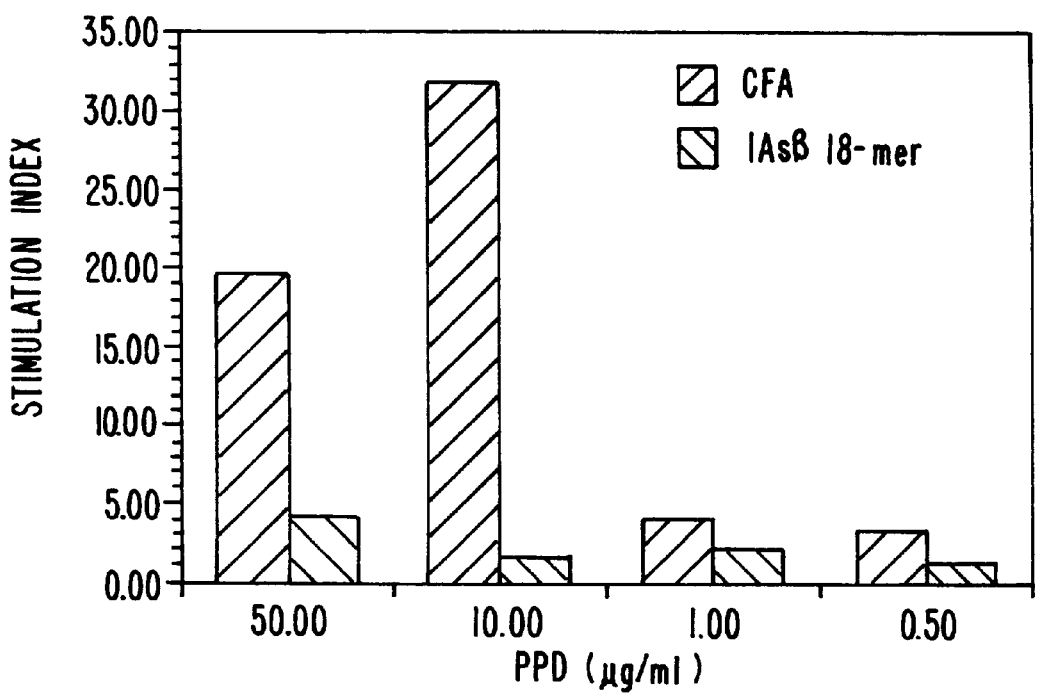

In order to determine if an antibody response to I-A$^s$β 18-mer peptide affects the development of immunity to soluble recall antigens, SJL mice were vaccinated with either I-A$^s$β 18-mer peptide in CFA, or CFA alone. 4 weeks later both groups receiver 400 µg of MBP in CFA. Ten days after receiving MBP, the regional lymph nodes were harvested and the proliferative responses to MBP and PPD (purified protein derivative of tuberculin) were determined. Mice that had received I-A$^s$β 18-mer peptide had a significantly lowered proliferative response to both MBP and PPD when compared to the control group that received CFA alone (FIG. 8).

EXAMPLE 4

This example demonstrates the manufacture of a Class II HLA DR4Dw4 β chain peptide vaccine for use against Rheumatoid Arthritis in humans.

While the primary immunodominant self-immunogen(s) are not known in RA, the disease is clearly associated with the MHC Class II molecules which present self-peptide antigens to Th-cells. In particular, 3 Class II haplotypes are most prevalent in RA: HLA-DR1; DR-4w4; and DR-4w14. Eighty to ninety percent of all RA patients carry one or more of these susceptibility alleles.

The active peptide in the vaccine is a synthetic N-acetylated peptide of 20 amino acid residues, representing residues 57–76 of the Class II HLA-DR4Dw4 β-chain. This sequence defines a predisposition to RA and also identifies the location of a three-dimensional structure which is adjacent to sites involved in autoantigenic-peptide binding (MHC "pocket") and T-cell receptor binding.

The synthesis of the peptide is accomplished by sequential assembly from C-terminus to N-terminus on a derivatized resin support. After completion of the coupling cycles and cleavage from the solid support with hydrogen fluoride (HF), the peptide is purified by column chromatography. DR4/1-Peptide amino acid sequence from N-terminus to C-terminus:

Acetyl-L-Asp-Ala-Glu-Tyr-Trp-Asn-Ser-Gln-Lys-Asp-Leu-Leu-Glu-Gln-Lys-Arg-Ala-Ala-Val-Asp (SEQ IS NO: 3).

Resin Chemistry

Approximately 3–5 kg of polystyrene (100–200 mesh, 1% divinylbenzene content) was combined with 30–40 L of 1,2-dichloroethane, 500–1000 g of p-toluoyl chloride, and 500–1000 g of aluminum chloride in a reaction vessel flushed with argon. The reaction proceeded at 0° C. for 15–30 minutes. The reaction was then brought to room temperature and allowed to proceed for an additional 12–36 hours. The resultant ketone resin was washed and filtered using methanol, USP Purified Water (water), and methylene chloride. A portion of the material was removed and examined by infrared spectroscopy to confirm structure.

The resin was next reductively aminated by adding 6–8 kg of ammonium formate, 20–30 L of nitrobenzene, 7–10 L of formamide, and 4–6 L of formic acid. While stirring, the mixture was brought to and maintained at about 170° C. for 48–72 hours. The aminated resin was washed and filtered using methanol and methylene chloride. A portion of the material was removed and examined as above.

The final step was hydrolysis of the aminated resin using ethanol under acidic conditions. The reduced resin was combined with 6–12 L of ethanol (EtOH) and 5–10 L of hydrochloric acid. While stirring, the reaction mixture was maintained at approximately 78° C. where mild refluxing occurred. The reaction was allowed to proceed overnight.

The completed p-Methyl Benzhydrylamine Resin (pMBHA-Rx) was washed and filtered using methanol, water, and methylene chloride. The filtered product was dried under vacuum at 40° C. A portion of the material was removed and examined with infrared spectroscopy to confirm structure.

Peptide synthesis

The DR4/1-peptide was produced by the solid-phase peptide synthesis of Merrifield (*Science*, 232:341 (1986)). The process entailed assembly of the peptide from the C-terminus to the N-terminus on the pMBHA-Rx solid support. Following assembly of the fully protected peptide, the peptide was cleaved from the support with concomitant deprotection of the side chain protecting groups.

The solid phase peptide synthesis employed chemistry compatible with tertiary-butyloxycarbonyl amino acids (Boc AA).

TABLE 3

The Boc-amino acids used for peptide synthesis

| Boc-Amino Acid | Full name |
| --- | --- |
| Boc-Asp | N-Boc-L-Aspartic Acid-β-Benzyl Ester |
| Boc-Ala | N-Boc-L-Alanine |
| Boc-Val | N-Boc-L-Valine |
| Boc-Arg | N-alpha-Boc-N-Tosyl-L-Arginine |
| Boc-Lys | N-alpha-Boc-N-epsilon-2-chlorobenzyloxycarbonyl-L-Lysine |
| Boc-Gln | N-alpha-Boc-L-Glutamine |
| Boc-Glu | N-Boc-L-Glutamic Acid-gamma-Benzyl Ester |
| Boc-Leu | N-Boc-L-Leucine-H$_2$0 |
| Boc-Asp | N-Boc-L-Aspartic Acid-β-Cyclohexyl Ester |
| Boc-Ser | N-Boc-O-Benzyl-L-Serine |
| Boc-Asn | N-alpha-Boc-L-Asparagine |
| Boc-Trp | N-Boc-L-Tryptophan |
| Boc-Tyr | N-Boc-O-(2-Bromobenzyloxycarbonyl)-L-Tyrosine |

The required amount of resin needed for the process was determined by the substitution of the resin:

$$\text{Amount of Resin (g)} = \frac{\text{Batch size (mmoles)}}{\text{Substitution (mmoles/g)}}$$

The calculated amount of resin was neutralized in a reaction vessel by washing successively with EtOH, DCM, and 10% DIEA in DCM for 1.5 minutes each.

Each Boc AA in the sequence was assigned a coupling cycle number corresponding to its position within the peptide chain. The required amount of each Boc AA was calculated to include a 3-fold excess to ensure completeness of the coupling reaction.

$$\text{Theoretical Amount of Boc-AA(g)} = \frac{(\text{mmoles required})(\text{excess})(\text{M.W.})}{1000}$$

All synthesis operations were conducted in Beckman System 990B or 990C synthesizers at ambient temperature. Nitrogen pressure was used throughout the process to facilitate solvent transfer and removal and to provide a dry, inert atmosphere for all reactions.

To begin synthesis, a three-fold excess of Boc-Asp was dissolved in the required amount of either dimethylformamide (DMF) or DCM, added to the reaction vessel and stirred for 1–5 minutes. An equimolar amount of the coupling agent, BOP, was added to the reaction vessel. The required amount of 10% DIEA in DCM was added and the reaction mixture was stirred for 90 minutes. In this manner, the Boc-Asp was coupled to the resin through its side chain. After the coupling period, the Asp-O-resin was washed with DCM and 10% DIEA in DCM.

The free amino function on the Asp-O-resin was then acetylated ("capped") by washing sequentially with 10% DIEA in DCM for 1.5 minutes and then with 10% acetic anhydride in DCM.

The acetylated Asp-O-resin was deprotected by washing sequentially with DCM for 1.5 minutes; 0.1% indole in 40% TFA in DCM for 1.5 minutes; 0.1% indole in 40% TFA in DCM for 30 minutes; and DCM for 1.5 minutes. This was followed by neutralization with dilute DIEA solution.

Successful coupling was determined with the Kaiser ninhydrin test. If the test was positive, coupling was repeated. Coupling could be repeated for a maximum of two times. If the second coupling was not successful, the peptide-resin was acetylated according to the process described above before proceeding to the next cycle. If the ninhydrin test was negative, the synthesis proceeded to the next cycle.

The above procedure was repeated for all coupling cycles to generate the 20 amino acid peptide.

After successfully coupling the last amino acid, the Boc-peptide-O-resin was deprotected by removing the N-terminal Boc group as before plus two additional one minute washes with EtOH and two additional one minute washes with DCM. This was followed by a ninhydrin test. If the test was negative, deprotection and washing were repeated. If the ninhydrin test was positive, terminal acetylation was performed.

The N-terminus of the peptide was acetylated by washing the peptide-resin successively with 10% DIEA in DCM for 1.5 minutes and 10% acetic anhydride in DCM for 5 minutes. This was followed by two 1.5 minute washes with DCM and a ninhydrin test. If the ninhydrin test was positive, the acetylation and washing processes were repeated.

The acetylated, side-chain protected, peptide-resin was removed from the reaction vessel and dried under vacuum for a minimum of 12 hours.

Before cleaving the peptide from the support, a 50% acetic acid (HOAc (aq)) solution was prepared for peptide extraction. An HF apparatus was assembled using a Kel-F reaction vessel and teflon valves and tubing.

The required amount of peptide-resin was weighed and transferred to the reaction vessel. The vessel was stirred with a teflon-coated magnetic stir bar. Anisole (1–2 mL/g peptide-resin) and 1,2-ethanedithiol were added to the reaction vessel to serve as scavengers by reacting with the carbonium ions produced during the cleavage process.

The reaction vessel was then securely attached to the HF apparatus and cooled with a dry ice/acetone bath for at least 5 minutes before proceeding. The HF apparatus was evacuated to 360–390 mm Hg with a vacuum pump. To ensure that the vacuum was maintained, the apparatus was observed for 10 minutes before proceeding with the HF reaction.

Once constant vacuum had been achieved, a volume of about 10 mL of HF per gram of peptide-resin was condensed into the reaction vessel. A standard ice bath kept at 0° C. replaced the dry ice/acetone bath. The reaction mixture was stirred at a moderate rate and allowed to proceed for 60 minutes.

Once the cleavage process was complete, the HF was evaporated from the reaction vessel into either a liquid nitrogen condensing vessel or a calcium oxide trap. After all of the HF and part of the anisole evaporated, the reaction vessel was disconnected from the HF apparatus.

Ten to twenty mL of anhydrous ethyl ether (ether) per gram of peptide-resin were added to the reaction vessel and stirred for 2–10 minutes. The contents of the reaction vessel were then transferred to a sintered glass funnel. Using water aspiration, the ether was removed from the peptide and resin mixture. The filter cake was washed in three batches, with 10–20 mL of ether per gram of peptide-resin.

The peptide was extracted from the resin by washing the filter cake three times, using 5–10 mL of 50% HOAC (aq) per gram of peptide-resin each washing.

The extracted, crude peptide was suspended in water and lyophilized. This material was weighed and stored at 2–8° C.

Chromatography of DR4/1-peptide

After cleavage and recovery, the crude DR4/1-peptide underwent purification to remove organic solvent residues and any incorrectly synthesized peptides. Purification of the crude peptide was accomplished by three chromatography processes: reverse phase chromatography, preparative HPLC, and ion exchange chromatography.

Reverse Phase Chromatography

The DR4\1-peptide was solubilized in 0.1% TFA in water. The peptide was applied to a 40–60 cm $C_{18}$ resin and eluted in 0–100% buffer A (0.1% TFA in 34% acetonitrile in water) over a 12–16 hour period. The flow rate was 3 mL/min with 12 mL fractions collected. The peptide was located by Thin Layer Chromatography (TLC) on selected fractions and the location of the peak confirmed by analytical HPLC. The appropriate fractions were pooled, frozen and lyophilized to remove the solvent.

Preparative HPLC

The lyophilized peptide was solubilized in either 0.1% TFA in water or 0.5 M $NH_4OAc$ in DMF. Preparative HPLC was performed with a Beckman 350 ($C_{18}$) column (10×250 mm) or equivalent. The peptide was eluted in 0–32% buffer B (0.1% TFA in 60% acetonitrile in water) for 30 minutes and then from 32–42% buffer B over 150 minutes. The flow rate was 4 mL/min with 6 mL fractions collected. The process was monitored by UV detection. The peptide peak was located by TLC and confirmed by analytical HPLC. The appropriate fractions were pooled, frozen and lyophilized.

Ion Exchange

The peptide was solubilized in acetic acid buffer and converted to the acetate salt by eluting the peptide with 5–10% acetic acid in water from a column packed with AG1X8 resin. The flow rate was 4 mL/min and 16 mL fractions collected. The peptide peak was found by TLC on selected fractions, and the location confirmed by analytical HPLC. The appropriate fractions were pooled, frozen, and lyophilized.

EXAMPLE 5

This example provides exemplary doses and formulations of an immunogenic MHC peptide for use in human vaccination.

Final Vaccine Package

The final vaccine package consists of: (1) the purified, lyophilized, DR4/1-peptide formulated in an acetate buffer, aseptically filtered, and filled in vials; (2) a moist heat-sterilized alum adjuvant filled in separate vials; and (3) a separate sterile mixing vial. Shortly before injecting the vaccine into a human patient, the peptide and adjuvant are diluted to the appropriate volume in the separate mixing vial.

Preparation of final vaccine dosage forms

The final dosage form is prepared by adding the alum adjuvant to the peptide and after gentle mixing, transferring the appropriate amount of peptide/alum mixture to the mixture vial and adding saline to a final volume of 2.0 mL. There are six dosage levels.

Preparation of the Peptide/Alum Mixture

The sterile DR4/1-Peptide Solution is formulated at the following concentration: 8 mg of peptide (lyophilized powder) in a solution volume of about 1.6 mL in 0.01 M sodium acetate, about pH 5.2, which has been sterilized by filtration.

The sterile alum adjuvant (Superfos, Denmark), is packaged in sealed vials and consists of aluminum hydroxide gel (alum) mixed with 0.25 M tris buffered saline to a final alum concentration of about 3.65 mg/mL. The pH is about 7.5. The alum adjuvant is sterilized by moist heat.

At least 30 minutes before use and not longer than 4 hours before use, 0.4 mL of Alum is aseptically withdrawn and added to the DR4/1-Peptide vial and restoppered. While at room temperature, the mixture should be gently swirled at T=0, T=15 min and at T=30 min. The vaccine mixture contains a total of 8000 mcg peptide and 1500 mcg Alum adjuvant in a total volume of 2.0 mL. Table 4 indicates the best mode for diluting the vaccine for the appropriate doses.

TABLE 4

Preparation of Vaccine Dosage Levels

| Dose Level | Concentration of Peptide and Alum | Volume of Peptide/Alum Mixture | Volume of Sterile Saline |
|---|---|---|---|
| 1 | 4000 mcg peptide, 750 mcg Alum/1.0 mL | 2.0 mL of undiluted mixture | 0.0 mL |
| 2 | 1300 mcg peptide, 240 mcg Alum/1.0 mL | 0.65 mL of undiluted mixture (dose level #1) | 1.35 mL |
| 3 | 1000 mcg peptide, 188 mcg Alum/1.0 mL | 0.5 mL of undiluted mixture | 1.5 mL |
| 4 | 400 mcg peptide, 75 mcg Alum/1.0 mL | 0.2 mL of undiluted mixture | 1.8 mL |
| 5 | 130 mcg peptide, 24 mcg Alum/1.0 mL | 0.2 mL of 1300 mcg/ml preparation (dose level #2) | 1.8 mL |
| 6 | 40 mcg peptide, 7.5 mcg Alum/1.0 mL | 0.2 mL of 400 mcg/ml preparation (dose level #5) | 1.8 mL |

Once the correct doses of vaccine have been achieved, 1.0 mL of the vaccine can then be injected intramuscularly into human patients.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A composition comprising an isolated immunogenic MHC polypeptide, wherein the immunogenic MHC polypeptide comprises a sequence from a hypervariable region of a human HLA Class II DR4Dw4 allele β chain associated with susceptibility to an autoimmune disease, and wherein said polypeptide is selected from the group consisting of:

a) a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4];

b) a fragment of the polypeptide of section (a) comprising at least 10 amino acid residues; and, c) a multimer of the polypeptide of section (a) or (b).

2. The composition of claim 1, wherein the immunogenic MHC polypeptide is a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4].

3. The composition of claim 2, wherein the polypeptide is acetylated at the amino terminus.

4. The composition of claim 1 wherein the immunogenic MHC polypeptide is a multimer of a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4].

5. The immunogenic peptide of claim 1 that is linked to a carrier polypeptide.

6. The immunogenic polypeptide of claim 5 wherein the carrier polypeptide is thyroglobulin, human serum albumin, tetanus toxoid, poly(lysine:glutamic acid), influenza, and hepatitis B virus core protein.

7. A pharmaceutical composition comprising a pharmaceutically acceptable excipient, an adjuvant and an immunogenic MHC polypeptide, wherein the immunogenic MHC polypeptide comprises a sequence from a hypervariable region of a human HLA Class II DR4Dw4 allele β chain associated with susceptibility to an autoimmune disease, and wherein said polypeptide is selected from the group consisting of:

a) a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4];

b) a fragment of the polypeptide of section (a) comprising at least 10 amino acid residues; and, c) a multimer of the polypeptide of section (a) or (b).

8. The composition of claim 7, wherein the immunogenic MHC polypeptide is a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4].

9. The composition of claim 8, wherein the polypeptide is acetylated at the amino terminus.

10. The composition of claim 7, wherein the immunogenic MHC polypeptide is a multimer of a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4].

11. The composition of claim 7, wherein the adjuvant is alum.

12. The immunogenic peptide of claim 7 that is linked to a carrier polypeptide.

13. The immunogenic polypeptide of claim 12 wherein the carrier polypeptide is thyroglobulin, human serum albumin, tetanus toxoid, poly(lysine:glutamic acid), influenza, and hepatitis B virus core protein.

14. A method of inhibiting a deleterious immune response in a patient with an autoimmune disease, the method comprising administering to the patient an immunologically effective amount of a pharmaceutical composition comprising an adjuvant and an immunogenic MHC polypeptide, wherein the immunogenic MHC polypeptide comprises a sequence from a hypervariable region of a human HLA Class II DR4Dw4 allele β chain associated with susceptibility to an autoimmune disease, wherein said polypeptide is selected from the group consisting of:

a) a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4];

b) a fragment of the polypeptide of section (a) comprising at least 10 amino acid residues; and, c) a multimer of the polypeptide of section (a) or (b).

15. The method of claim 14, wherein the immunogenic MHC polypeptide is a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4].

16. The method of claim 15, wherein the polypeptide is acetylated at the amino terminus.

17. The method of claim 14, wherein the immunogenic MHC polypeptide is a multimer of a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4].

18. The method of claim 17, wherein the adjuvant is alum.

19. The method of claim 17, wherein the immunogenic peptide is linked to a carrier polypeptide.

20. The method of claim 19, wherein the carrier polypeptide is thyroglobulin, human serum albumin, tetanus toxoid, poly(lysine:glutamic acid), influenza, and hepatitis B virus core protein.

21. The method of claim 14 wherein the autoimmune disease is rheumatoid arthritis.

22. The method of claim 15 wherein the autoimmune disease is rheumatoid arthritis.

23. A method of treating an autoimmune disease in a patient, the method comprising administering to the patient an immunologically effective amount of a pharmaceutical composition comprising an adjuvant and an immunogenic MHC polypeptide, wherein the immunogenic MHC polypeptide comprises a sequence from a hypervariable region of a human HLA Class II DR4Dw4 allele β chain associated with susceptibility to an autoimmune disease, and wherein said polypeptide is selected from the group consisting of:

a) a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4];

b) a fragment of the polypeptide of section (a) comprising at least 10 amino acid residues; and, c) a multimer of the polypeptide of section (a) or (b).

24. The method of claim 23, wherein the administration is parenteral.

25. The method of claim 23, wherein the immunogenic MHC polypeptide is administered prophylactically.

26. The method of claim 23, wherein the immunogenic MHC polypeptide is a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4].

27. The method of claim 26, wherein the polypeptide is acetylated at the amino terminus.

28. The method of claim 23, wherein the immunogenic MHC polypeptide is a multimer of a 20 amino acid residue polypeptide with the sequence Asp-Ala-Glu-Tyr-Trp-Asn-Ser-Gln-Lys-Asp-Leu-Leu-Glu-Gln-Lys-Arg-Ala-Ala-Val-Asp [SEQ ID NO: 4].

29. The method of claim 23, wherein the adjuvant is alum.

30. The method of claim 23, wherein the administration is parenteral.

31. The method of claim 23, wherein the immunogenic MHC polypeptide is administered prophylactically.

32. The method of claim 23, wherein the immunogenic peptide is linked to a carrier polypeptide.

33. The method of claim 32, wherein the carrier polypeptide is thyroglobulin, human serum albumin, tetanus toxoid, poly(lysine:glutamic acid), influenza, and hepatitis B virus core protein.

34. The method of claim 23, wherein the patient has rheumatoid arthritis.

35. The method of claim 26, wherein the patient has rheumatoid arthritis.

* * * * *

UNITED STATES PATENT AND TRADEMARK OFFICE
CERTIFICATE OF CORRECTION

PATENT NO. : 6,045,796
DATED : April 4, 2000
INVENTOR(S) : Subramaniam Sriram et al It is certified that error appears in the above-identified patent and that said Letters Patent is hereby corrected as shown below:

Column 20, Line 2, please delete "SEQ IS NO:3" and insert --SEQ ID NO:3--.

Column 25, in the Sequence Listing Information for SEQ ID NO: 3, residue #10 "Asn" should be --Asp--.

Column 25, in the Sequence Listing Information for SEQ ID NO: 4, residue #10 "Asn" should be --Asp--.

Signed and Sealed this

Twenty-fourth Day of April, 2001

Attest:

NICHOLAS P. GODICI

*Attesting Officer*    *Acting Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl-alanine"

(ix) FEATURE:
        (A) NAME/KEY: Modified-site
        (B) LOCATION: 18
        (D) OTHER INFORMATION: /product= "OTHER"
            /note= "Xaa = Theoninamide"

(xi) SEQUENCE DESCRIPTION: SEQ ID NO:1:

```
Xaa Glu Tyr Tyr Asn Lys Gln Tyr Leu Glu Gln Thr Arg Ala Glu Leu
1               5                   10                  15

Asp Xaa
```

(2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

```
Tyr Tyr Asn Lys Gln Tyr Leu Glu Gln Thr
1               5                   10
```

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl-asparagine"

(xi) SEQUENCE DESCRIPTION: SEQ ID NO:3:

```
Xaa Ala Glu Tyr Trp Asn Ser Gln Lys Asn Leu Leu Glu Gln Lys Arg
1               5                   10                  15

Ala Ala Val Asp
            20
```

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Asp Ala Glu Tyr Trp Asn Ser Gln Lys Asn Leu Leu Glu Gln Lys Arg
1               5                   10                  15

Ala Ala Val Asp
            20
```